US007951398B2

(12) United States Patent
Dietrich et al.

(10) Patent No.: US 7,951,398 B2
(45) Date of Patent: *May 31, 2011

(54) PHARMACEUTICAL PREPARATION COMPRISING AN ACTIVE DISPERSED ON A MATRIX

(75) Inventors: Rango Dietrich, Constance (DE); Rudolf Linder, Constance (DE); Hartmut Ney, Constance (DE)

(73) Assignee: Nycomed GmbH, Constance (DE)

(*) Notice: Subject to any disclaimer, the term of this patent is extended or adjusted under 35 U.S.C. 154(b) by 973 days.

This patent is subject to a terminal disclaimer.

(21) Appl. No.: 11/642,621

(22) Filed: Dec. 21, 2006

(65) Prior Publication Data

US 2007/0122474 A1    May 31, 2007

Related U.S. Application Data

(63) Continuation of application No. 10/433,398, filed as application No. PCT/EP01/14307 on Dec. 6, 2001, now Pat. No. 7,175,854.

(30) Foreign Application Priority Data

Dec. 7, 2000    (EP) ..................... 00126847

(51) Int. Cl.
*A61K 9/20* (2006.01)

(52) U.S. Cl. ........ 424/464; 424/484; 424/489; 424/465; 424/469

(58) Field of Classification Search .................. 424/464
See application file for complete search history.

(56) References Cited

U.S. PATENT DOCUMENTS

| | | | |
|---|---|---|---|
| 3,065,142 | A | 11/1962 | Antonides |
| 4,006,227 | A | 2/1977 | Gallegos et al. |
| 4,464,372 | A | 8/1984 | Bristol et al. |
| 4,833,149 | A | 5/1989 | Press |
| 5,041,442 | A | 8/1991 | Romero et al. |
| 5,188,838 | A | 2/1993 | Deleuil et al. |
| 5,380,532 | A | 1/1995 | Deleuil et al. |
| 5,429,824 | A | 7/1995 | June |
| 5,665,730 | A | 9/1997 | Senn-Bilfinger et al. |
| 5,677,302 | A | 10/1997 | Karimian et al. |
| 5,719,161 | A | 2/1998 | Rainer |
| 5,762,953 | A | 6/1998 | Venkateshwaran |
| 6,114,537 | A | 9/2000 | Karimian et al. |
| 6,124,313 | A | 9/2000 | Grundler et al. |
| 6,231,885 | B1 | 5/2001 | Carrara |
| 7,147,869 | B2 * | 12/2006 | Dietrich et al. ........... 424/466 |
| 7,175,854 | B2 * | 2/2007 | Dietrich et al. ........... 424/464 |
| 7,357,943 | B2 * | 4/2008 | Linder et al. ........... 424/442 |

FOREIGN PATENT DOCUMENTS

| | | |
|---|---|---|
| DE | 30 11 490 A1 | 3/1981 |
| DE | 36 22 036 A1 | 1/1987 |
| DE | 39 17 232 A1 | 11/1990 |
| DE | 691 01 493 T2 | 8/1994 |
| DE | 199 25 710 A1 | 12/2000 |
| EP | 0 033 094 B1 | 8/1981 |
| EP | 0 068 378 B1 | 1/1983 |
| EP | 0 120 589 B1 | 10/1984 |
| EP | 0 125 756 A2 | 11/1984 |
| EP | 0 165 545 A2 | 12/1985 |
| EP | 0 204 285 A1 | 12/1986 |
| EP | 0 228 006 A1 | 7/1987 |
| EP | 0 259 174 A1 | 3/1988 |
| EP | 0 261 912 A2 | 3/1988 |
| EP | 0 264 883 A2 | 4/1988 |
| EP | 0 266 890 A1 | 5/1988 |
| EP | 0 268 989 B1 | 6/1988 |
| EP | 0 307 078 B1 | 3/1989 |
| EP | 0 308 917 A2 | 3/1989 |
| EP | 0 330 485 A1 | 8/1989 |
| EP | 0 368 158 A1 | 5/1990 |
| EP | 0 387 821 B1 | 9/1990 |
| EP | 0 393 926 B1 | 10/1990 |
| EP | 0 399 267 A2 | 11/1990 |
| EP | 0 438 359 A1 | 7/1991 |
| EP | 0 509 974 B1 | 10/1992 |
| EP | 0 535 529 B1 | 4/1993 |
| EP | 0 537 532 B1 | 4/1993 |
| EP | 0 563 024 B1 | 9/1993 |
| JP | 2-270873 | 11/1990 |
| JP | 3-31280 | 2/1991 |
| JP | 3-284622 | 12/1991 |
| JP | 3-284686 | 12/1991 |
| JP | 5-271070 | 10/1993 |
| JP | 9-59152 | 3/1997 |

(Continued)

OTHER PUBLICATIONS

Hafner, et al., "Additive effects of phosphodiesterase-4 inhibition on effecs of rSP-C surfactant", *AM J Respir Crit Care Med*. vol. 161, No. 5, pp. 1495-1500, (2000).
Lewis, et al., "The physical and chemical stability of suspensions of sustained-released diclofenac microspheres", *J. Microencapsulation*, vol. 15, No. 5, pp. 555-567, (1998).
Safety Data Sheet, Crodesta SL40, HB03791, Aqua and Sucrose Cocoate and Alcohol, Croda Europe Ltd., 5 pages, (2004).
Safety Data Sheet, Crodesta F20, HB03668, Sucrose Distearate, Croda Europe Ltd., 5 pages (2008).
Safety Data Sheet, Crodesta F50, HB03669, Sucrose Distearate, Croda Europe Ltd., 5 pages (2005).
Safety Data Sheet, Crodesta F10, HB03671, Sucrose Distearate, Croda Europe Ltd., 5 pages, (2005).
Safety Data Sheet, Crodesta F110, HB03722, Sucrose Stearate and Sucrose Distearate, Croda Europe Ltd., 5 pages, (2005).
Safety Data Sheet, Crodesta F160, HB03750, Sucrose Stearate, Croda Europe Ltd., 4 pages, (2005).

*Primary Examiner* — Jake M. Vu
(74) *Attorney, Agent, or Firm* — The Nath Law Group; Joshua B. Goldberg; Sheldon M. McGee

(57) ABSTRACT

The present invention relates to the field of pharmaceutical technology and describes a novel advantageous preparation for an active ingredient. The novel preparation is suitable for producing a large number of pharmaceutical dosage forms. In the new preparation, an active ingredient is present essentially uniformly dispersed in an excipient matrix composed of one or more excipients selected from the group of fatty alcohols, triglycerides, partial triglycerides and fatty acid esters.

20 Claims, No Drawings

FOREIGN PATENT DOCUMENTS

| | | |
|---|---|---|
| JP | 11/152224 | 6/1999 |
| JP | 2000-86502 | 3/2000 |
| JP | 2000-516633 | 12/2000 |
| WO | 89/00570 | 1/1989 |
| WO | 91/14677 | 10/1991 |
| WO | 91/17164 | 11/1991 |
| WO | 91/18887 | 12/1991 |
| WO | 92/06979 | 4/1992 |
| WO | 92/12969 | 8/1992 |
| WO | 92/21328 | 12/1992 |
| WO | 93/08190 | 4/1993 |
| WO | 93/12090 | 6/1993 |
| WO | 93/12090 A1 | 6/1993 |
| WO | 93/15055 | 8/1993 |
| WO | 93/15056 | 8/1993 |
| WO | 93/15071 | 8/1993 |
| WO | 94/14795 | 7/1994 |
| WO | 94/24130 | 10/1994 |
| WO | 97/25030 | 7/1997 |
| WO | 98/07400 | 2/1998 |
| WO | 00/10999 | 3/2000 |

* cited by examiner

PHARMACEUTICAL PREPARATION COMPRISING AN ACTIVE DISPERSED ON A MATRIX

This application is a continuation application of U.S. Ser. No. 10/433,398, filed Sep. 11, 2003, now U.S. Pat. No. 7,175,854, which was filed under 35 U.S.C. 371 from PCT Application No. PCT/EP01/14307, filed Dec. 6, 2001.

TECHNICAL FIELD

The present invention relates to the field of pharmaceutical technology and describes a novel advantageous preparation for an active ingredient. The novel preparation is suitable for the production of a large number of pharmaceutical dosage forms.

BACKGROUND ART

In order to achieve particular properties of a dosage form, such as, for example, taste masking in the case of active ingredients with an unpleasant taste, resistance to gastric juice in the case of acid-labile active ingredients or controlled release of an active ingredient, normally active ingredient pellets are provided with an appropriate functional coating. If such coated pellets are then further processed to dosage forms, for example shaped to tablets by compression with excipients, there is a risk that the coating is damaged and thus the functionality is at least partly lost again.

DESCRIPTION OF THE INVENTION

It is an object of the present invention to provide a preparation for active ingredients which is able to retain a desired functionality and can be further processed to a large number of pharmaceutical process forms with negligible impairment of a given functionality.

It has now been found, surprisingly, that this object is achieved by a preparation in which an active ingredient is essentially uniformly dispersed in an excipient matrix composed of one or more excipients selected from the group of fatty alcohol, triglyceride, partial glyceride and fatty acid ester.

The invention therefore relates to a preparation in which an active ingredient is essentially uniformly dispersed in an excipient matrix composed of one or more excipients selected from the group of fatty alcohol, triglyceride, partial glyceride and fatty acid ester.

It has further been found that particularly advantageous preparations can be obtained by adding solid paraffin to the excipient matrix. The invention therefore relates further to a preparation in which an active ingredient is essentially uniformly dispersed in an excipient matrix composed of at least one solid paraffin together with one or more excipients selected from the group of fatty alcohol, triglyceride, partial glyceride and fatty acid ester.

The invention further relates to preparations in which an active ingredient is essentially uniformly dispersed i) in an excipient matrix composed of a mixture comprising at least one fatty alcohol and at least one solid paraffin, ii) in an excipient matrix comprised of a mixture comprising at least one triglyceride and at least one solid paraffin, iii) in an excipient matrix composed of a mixture comprising at least one partial glyceride and at least one solid paraffin or iv) in an excipient matrix composed of a mixture comprising at least one fatty acid ester and at least one solid paraffin.

Further subject matters are evident from the claims.

The preparations for the purpose of the invention preferably comprise numerous individual units in which at least one active ingredient particle, preferably a large number of active ingredient particles, is present in an excipient matrix composed of the excipients of the invention (also referred to as active ingredient units hereinafter). The active ingredient is preferably essentially uniformly dispersed, in particular homogeneously dispersed or dissolved, in the excipient matrix. A preparation preferably comprises microspheres.

The preparations of the invention are distinguished in particular by high stability, a release of active ingredient which can be controlled by the particle size and composition of the matrix, good flow characteristics, good compressibility and by a uniform delivery of active ingredient. In the case of acid-labile active ingredients it is moreover possible to achieve, through choice of the matrix excipients, an acid resistance so that it is possible in the case of oral forms to dispense with an acid-resistant coating (enteric coating). In the case of active ingredients which have an unpleasant taste or, for example, show a local anesthetic effect in the mouth after administration, it has been observed that an unpleasant taste of the active ingredient can be masked, and anesthetic effects in the mouth can be avoided, by preparations of the invention. It is particularly worthy of mention that the preparations of the invention can be further processed to a large number of pharmaceutical dosage forms without thereby losing a given functionality (such as taste masking, resistance to gastric juice, slowing of release). Thus, for example, on compression of the active ingredient units of the invention no or negligible loss of functionality is observed even if deformation of the active ingredient units occurs. In contrast to this, with conventional pellets, which normally have a functional coating (such as taste masking, resistance to gastric juice, slowing of release), a certain degree of damage to the coating and thus to the functionality is observed on further processing to dosage forms, for example on compression to tablets. This may also lead in some cases to active ingredient being released in an unwanted way.

The particle size of the individual units is advantageously less than or equal to 2 mm, preferably 50-800 µm, particularly preferably 50-700 µm and very particularly preferably 50-600 µm. Preference is given to microspheres of a particle size of 50-500 µm, particularly preferably of 50-400 µm. Particular preference is given to monomodal microspheres with a particle size of 50-400 µm, particularly of 50-200 µm.

Active ingredients of the invention are, in particular, active pharmaceutical ingredients. Examples of active ingredients which may form part of the preparations of the invention are, in particular, the active pharmaceutical ingredients mentioned below:

Adrenergics:
apraclonidine; brimonidine; dapiprazole; deterenol; dipivefrin; dopamine; ephedrine; esproquin; etafedrine; hydroxyamphetamine; levonordefrin; metaraminol; norepinephrine; oxidopamine; phenylpropanolamine; prenalterol; propylhexedrine; pseudoephedrine.

Adrenocorticosteroids:
ciprocinonide; desoxycorticosterone acetate; desoxycorticosterone pivalate; dexamethasone acetate; fludrocortisone acetate; flumoxonide; hydrocortisone hemisuccinate; methylprednisolone hemisuccinate; naflocort; procinonide; timobesone acetate; tipredane.

Agents to Prevent Alcohol Abuse:
disulfiram, acamprosate, milnacipran, fomepizole, lazabemide, nadide; nitrefazole; sunepitron.

Aldosterone Antagonists:

canrenoate; canrenone; dicirenone; mexrenoate; prorenoate; spironolactone, epostane, mespirenone; oxprenoate, spirorenone, spiroxasone, prorenone, eplerenone.

Amino Acids:

alanine; aspartic acid; cysteine; histidine; isoleucine; leucine; lysine; methionine; phenylalanine; proline; serine; threonine; tryptophan; tyrosine; valine.

Active ingredients for Ammonium Detoxification:

arginine; arginine glutamate; arginine hydrochloride; glutamic acid;

Anabolics:

androstanolone, bolandiol dipropionate; bolasterone; boldenone undecylenate; bolenol; bolnantalate; ethylestrenol; metenolone acetate; metenolone enanthate; bolazine; mesteronole; metandienone; nandrolone; oxandrolone; prasterone; stanozolone; tiomesterone; clostebol; mibolerone; nandrolone cyclotate; norbolethone; quinbolone; stenbolone acetate; tibolone; zeranol.

Analeptics:

modafinil; amineptine; endomide; etamivan; fenoxypropazine; fenozolone; hexapradol; nialamide; nicethamide.

Analgesics:

acetaminophen; alfentanil; aminobenzoate; aminobenzoate; anidoxime; anileridine; anileridine; anilopam; anirolac; antipyrine; aspirin; benoxaprofen; benzydamine; bicifadine hydrochloride; brifentanil; bromadoline; bromfenac; buprenorphine; butacetin; butixirate; butorphanol; butorphanol; carbamazepine; carbaspirin calcium; carbiphene; carfentanil; ciprefadol succinate; ciramadol; ciramadol; clonixeril; clonixin; codeine; codeine phosphate; codeine sulfate; conorphone; cyclazocine; dexoxadrol; dexpemedolac; dezocine; diflunisal; dihydrocodeine; dimefadane; dipyrone; doxpicomine; drinidene; enadoline; epirizole; ergotamine tartrate; ethoxazene; etofenamate; eugenol; fenoprofen; fenoprofen calcium; fentanyl citrate; floctafenine; flufenisal; flunixin; flunixin meglumine; flupirtine; fluproquazone; fluradoline; flurbiprofen; hydromorphone; ibufenac; indoprofen; ketazocine; ketorfanol; ketorolac; letimide; levomethadyl acetate; levomethadyl acetate hydrochloride; levonantradol; levorphanol; lofemizole; lofentanil oxalate; lorcinadol; lomoxicam; magnesium salicylate; mefenamic acid; menabitan; meperidine; meptazinol; methadone; methadyl acetate; methopholine; methotrimeprazine; metkephamid acetate; mimbane; mirfentanil; molinazone; morphine sulfate; moxazocine; nabitan; nalbuphine; nalmexone; namoxyrate; nantradol; naproxen; naproxen; naproxol; nefopam; nexeridine; noracymethadol; ocfentanil; octazamide; olvanil; oxetorone; oxycodone; oxycodone; oxycodone terephthalate; oxymorphone; pemedolac; pentamorphone; pentazocine; pentazocine; phenazopyridine; phenyramidol; picenadol; pinadoline; pirfenidone; piroxicam olamine; pravadoline; prodilidine; profadol; propiram; propoxyphene; propoxyphene napsilate; proxazole; proxorphan; pyrroliphene; remifentanil; salcolex; salethamide maleate; salicylamide; salicylate meglumine; salsalate; salicylate; spiradoline; sufentanil; sufentanil; talmetacin; talniflumate; talosalate; tazadolene; tebufelone; tetrydamine; tifurac; tilidine; tiopinac; tonazocine; tramadol; trefentanil; trolamine; veradoline; verilopam; volazocine; xorphanol; xylazine; zenazocine mesilate; zomepirac; sucapsalcin.

Androgens:

androstanolone; fluoxymesterone; mestanolone; mesterolone; metandienone; methyltestosterone; nandrolone decanoate; nandrolone phenpropionate; nisterime; oxandrolone; oxymesterone; oxymetholone; penmesterol; prasterone; silandrone; stanozolol; testosterone; testosterone cypionate; testosterone enanthate; testosterone ketolaurate; testosterone phenylacetate; testosterone propionate; trestolone.

Anesthetic Additives:

sodium oxibate.

Anesthetics (Non-Inhalation):

alfaxalone; amolanone; etoxadrol; fentanyl; ketamine; levoxadrol; methitural; methohexital; midazolam; minaxolone; propanidid; propoxate; pramoxine; propofol; remifentanyl; sufentanyl; tiletamine; zolamine.

Anesthetics (Local):

ambucaine; amoxecaine; amylocaine; aptocaine; articaine; benoxinate; benzyl alcohol; benzocaine; betoxycaine; biphenamine; bucricaine; bumecaine; bupivacaine; butacaine; butamben; butanilicaine; carbizocaine; chloroprocaine clibucaine; clodacaine; cocaine; dexivacaine; diamocaine; dibucaine; dyclonine; elucaine; etidocaine; euprocin; fexicaine; fomocaine; heptacaine; hexylcaine; hydroxyprocaine; hydroxytetracaine; isobutamben; ketocaine; leucinocaine; lidocaine; mepivacaine; meprylcaine; octocaine; orthocaine; oxethacaine; oxybuprocaine; parabutoxycaine; phenacaine; pinoicaine; piperocaine; piridocaine; polidocanol; pramocaine; prilocaine; procaine; propanocaine; propipocaine; propoxycaine; proxymetacaine; pyrrocaine; quatacaine; quinisocaine; risocaine; rodocaine; ropivacaine; salicyl alcohol; suicaine; tetracaine; trapencaine; trimecaine.

Appetite Suppressants:

amfepramone; amfetamine; aminorex; amfecloral; anisacril; benzfetamine; chlorphentermine; clobenzorex; cloforex; clominorex; clortermine; dexamfetamine; dexfenfluramine; difemetorex; etilamfetamine; etolorex; fenbutrazate; fencamfamin; fenfluramine; fenisorex; fenproporex; fludorex; fluminorex; formetorex; furfenorex; imanixil; indanorex; levamfetamine; levofacetoperane; levofenfluramine; levopropylhexedrine; mazindol; mefenorex; metamfepramone; morforex; norpseudoephedrine; orlistat; ortetamine; oxifentorex; pentorex; phendimetrazine; phenmetrazine; phentermine; picilorex; satietine; setazindol; sibutramine; triflorex; trifluorex.

Anthelmintics:

abamectin; albendazole; albendazole oxide; amidantel; amoscanate; antafenite; antazonite; anthelmycin; antholimine; bephenium hydroxynaphthoate; bidimazium iodide; bisbendazole; bithionoloxide; bitoscanate; bromoxanide; brotianide; bunamidine; butamisole; butonate; cambendazole; carbantel; ciclobendazole; clioxanide; closantel; dexamisole; diamfenetide; dichlorvos; diethylcarbamazine; dimantine; diphenan; doramectin; dribendazole; eprinomectin; epsiprantel; etibendazole; febantel; fenbendazole; flubendazole; flurantel; ftalofyne; furodazole; haloxon; hexylresorcinol; imcarbofos; ivermectin; kainic acid; mebendazole; metrifonate; metyridine; morantel; moxidectin; naftalofos; netobimin; niclofolan; niclosamide; nitramisole; nitrodan; nitroscanate; nitroxinil; oltipraz; ontianil, oxantel oxfendazole; oxibendazole; oxyclozanide; parbendazole; pexantel; piperamide; piperazine adipate; piperazine calcium edetate; piperamide praziquantel; proclonol; pyrantel pamoate; pyrantel tartrate; pyrvinium pamoate; rafoxanide; resorantel; salantel; spirazine; stilbanzium iodide; subendazole; tetramisole; thenium closilate; thiofuradene; tiabendazole; ticarbodine; tioxidazole; triclabendazole; triclofenol piperazine; uredofos; vincofos; zilantel.

Acne Therapeutics:

adapalene; adelmidrol; benzoyl peroxide; betacarotene; cioteronel; delanterone; cyproterone; doretinel; erythromycin salnacedin; etretinate; fumaric acid; halofuginonen; inocoterone acetate; isotretinoin; linolenic acid; manoalide;

masoprocol; mitotane; motretinide; namirotene; rosterelone; sumarotene; tazarotene; tematotene; tioxolone; topterone; tradecamide; tretinoin; triadimenol; zearalenone; zeranol; zimidoben.

Bronchodilators:
acefylline; azaspirium chloride; bambuterol; bamifylline; bitolterol; broxaterol; butaprost; carbuterol; cipamfylline; colterol; doxaprost; doxofylline; dyphylline; enprofylline; ephedrine; eprozinol; etanterol; fenspiride; flutropium bromide; formoterol; guaithylline; hexoprenaline; Hoku-81; hoquizil; imoxiterol; ipragratine; ipratropium bromide; isoetharine; isoproterenol; levosalbutamol; mabuterol; mequitamium iodide; metaproterenol; mexafylline; nardeterol; nestifylline; nisbuterol; picumeterol; piquizil; pirbuterol; procaterol; reproterol; RO-24-4736; quazodine; quinterenol; racepinephrine; reproterol; rimiterol; salbutamol; salmeterol; salmeterol xinafoate; sevitropium mesilate; soterenol; sulfonterol; suloxifen; TA-2005; theophylline; terbutaline; theophylline ethylenediamine; tiaramide; tipetropium bromide; tretoquinol; tulobuterol; zindotrine; zinterol.

Beta-Blockers:
acebunolol; adaprolol; afurolol; alprenolol; alprenoxime; ancarolol; arnolol; arotinolol; atenolol; befunolol; benzodioxine; betaxolol; bevantolol; bisoprolol; bormetolol; bopindolol; bornaprolol; brefonalol; bucumolol; bufetolol; bufuralol; bunitrolol; bunolol; bupranolol; butaxamine; butidrine; burocrolol; butofilolol; carazolol; carteolol; carvedilol; celiprolol; cetamolol; cicloprolol; cinamolol; cloranolol; cyanopindolol; dalbraminol; dexpropranolol; diacetolol; dichlorisoproterenol; dilevalol; draquinolol; dropranolol; ecastolol; epanolol; ericolol; esatenolol; esmolol; exaprolol; falintolol; flestolol; flusoxolol; hydroxycarteolol; hydroxytertatolol; ICI-118551; idropranolol; indenolol; indopanolol; iprocrolol; isamoltan; labetalol; landiolol; levobetaxolol; levobunolol; levocicloprolol; levomoprolol; medroxalol; mephenoxalone; mepindolol; metalol; metipranolol; metoprolol; mindodilon; moprolol; nadolol; nadoxolol; nafetolol; napitane; nebivolol; neraminol; nifenalol; nipradilol; oberadilol; oxanamide; oxprenolol; pacrinolol; pafenolol; pamatolol; pargolol; parodilol; penbutolol; penirolol; PHQA-33; pindolol; pirepolol; practolol; prenalterol; primidolol; procinolol; pronetalol; propacetamol; propranolol; ractopamine; ridazolol; ronactolol; soquinolol; sotalol; TA-2005; talinolol; tazolol; teoprolol; tertatolol; terthianolol; tienoxolol; tilisolol; timolol; tiprenolol; tolamolol; toliprolol; tribendilol; trigevolol; xamoterol; xibenolol; Y-12541; ZAM1-1305.

Adrenergic Agonists:
betanidine; bretylium tosilate; cromanidine; debrisoquine; ethomoxane; guabenxan; guanabenz; guanacline; guanadrel; guanazodine; guancidine; guanclofine; guanethidine; guanfacine; guanisoquine; guanoclor; guanoctine; guanoxabenz; guanoxan; guanoxyfen; olmidine; piperoxan; pyroxamidine; solypertine; spirgetine.

Alpha1 Antagonists:
abanoquil; adozelesin; alfuzosin; amosulalol; benoxathian; bunazosin; CI-926; DL-017; dapiprazole; dihydroergotamine mesilate; doxazosin; euigenodilol; fenspiride; GI-231818; GYKI-12743; GYKI-16084; indoramine; metazosin; MK-912; monatepil; naftopidil; neldazosin; nesapidil; nicergoline; pelanserin; peradoxime; peraquinsine; peratizole; perbufylline; phendioxan; phenoxybenzamine; phentolamine; podilfen; prazosin; quinazosin; RS-97078; proroxane; sertindole; SGB-1534; SL-89.0591; tamsulosin; tedisamil; terazosin; tibalosin; tiodazosin; tolazoline; trimazosin; upidosin; urapidil; yohimbine; zolertine.

ACE Inhibitors:
alacepril; benazepril; benazeprilat; BMS-189921; BRL-36378; captopril; ceronapril; CGS-13928C; cilazapril; cilazaprilat; dehydrocaptopril; delapril; enalapril; enalaprilat; EU-4867; EXP-7711; fasidotril; fosinopril; fosinoprilat; idrapril; imidapril; imidaprilat; indolapril; libenzapril; lisinopril; mixanpril; moexipril; moexiprilat; moveltipril; omapatrilat; orbutopril; pentopril; perindopril; perindoprilat; pivopril; quinapril; quinaprilat; ramipril; rentiapril; sampatrilat; SCH-54470; spirapril; spiraprilat; temocapril; temocaprilat; teprotide; trandolapril; trandolaprilat; utibapril; utibaprilat; Z-13752A; zabicipril; zofenopril; zofenoprilat.

Renin Antagonists
CGP-38560; ciprokiren; CP-108671; enalkiren; ES-6864; FK-906; remikiren; terlakiren; zankiren.

Antiallergics Such as PDE Inhibitors:
arofylline; atizoram, AWD-12-281 (N-(3,5-dichloro-4-pyridinyl)-2-[1-(4-fluorobenzyl)-5-hydroxy-1H-indol-3-yl]-2-oxoacetamide); BAY-19-8004 (ethanesulfonic acid 2-(2,4-dichlorophenylcarbonyl)-3-ureidobenzofuran-6-yl ester); benafentrine; CC-1088; CDC-801 (β-[3-(cyclopentyloxy)-4-methoxyphenyl]-1,3-dihydro-1,3-dioxo-2H-isoindole-2-propanamide); CDC-998; CI-1018; cilomilast (cis-[4-cyano-4-(3-cyclopentyloxy-4-methoxyphenyl)cyclohexane-1-carboxylic acid); cilostazol; cipamfylline (8-amino-1,3-bis (cyclopropylmethyl)xanthine); D-4396; D-4418 [N-(2,5-dichloro-3-pyridinyl)-8-methoxy-5-quinoline-carboxamide]; darbufelone; denbufylline; ER-21355; filaminast; ibudilast; IC-485; indolidan; laprafylline; lixazinone; MESOPRAM [(−)-(R)-5-(4-methoxy-3-propoxyphenyl)-5-methyloxazolidin-2-one]; nitraquazone; NM-702; olprinone; ORG-20241 (4-(3,4-dimethoxyphenyl)-N2-hydroxythiazole-2-carboxamidine); piclamilast; pumafentrine ((−)-cis-9-ethoxy-8-methoxy-2-methyl-1,2,3,4,4a,10b-hexahydro-6-(4-diisopropylaminocarbonylphenyl)benzo[c][1,6]-naphthyridine); quazinone; RO-15-2041; roflumilast (3-(cyclopropylmethoxy)-N-(3,5-dichloro-4-pyridyl)-4-(difluoromethoxy)-benzamide); rolipram; SCH-351591; SH-636; tibenelast (5,6-diethoxybenzo[b]thiophene-2-carboxylic acid); tolafentrine; trequinsin; V-11294A (3-[[3-(cyclopentyloxy)-4-methoxyphenyl]methyl]-N-ethyl-8-(1-methylethyl)-3H-purin-6-amine); YM-58997 (4-(3-bromophenyl)-1-ethyl-7-methyl-1,8-naphthyridin-2(1H)-one); YM-976 (4-(3-chlorophenyl)-1,7-diethylpyrido[2,3-d]pyrimidin-2(1H)-one); zardaverine.

Other Antiallergics for Asthma Treatment:
ablukast; atreleuton; bunaprolast; cinalukast; crornitrile; cromolyn; FPL-55712; iralukast; isamoxole; ketotifen; L-648051; levcromakalim; lodoxamide ethyl; lodoxamide tromethamine; montelukast; oxarbazole; piriprost; pirolate; pobilukast; pranlukast; ritolukast; sulukast; tiaramide; tibenelast; tomelukast; verlukast; verofylline; zafirlukast; zileuton.

Other Antiallergics (for Example Leukotriene Antagonists):
acitazanolast; acrivastine; alinastine; altoqualine; amlexanox; andolast; astemizole; ataquimast; azatadine; azelastine; bamipine; barmastine; batebulast; BAY-X-1005; BAY-X-7195; bepiastine; bepotastine; BIIL-284; bilastine; binizolast; buclizine; bunaprolast; cabastine; carebastine; cetirizine; CI-959; ciproxifan; clemastine; CMI-977; cromoglicic acid; cromolyn natrium; dametralast; desloratadine; dimenhydrinate; diphenhydramine; doqualast; dorastine; E-4704; efletirizine; emedastine; enofelast; enoxamast; ebastine; eclazolast; epinastine; fexofenadine; flezelastine; HSR-609; KCA-757; levocabastine; levocetirizine; linetastine; loratadine; LY-293111; mapinastine; mequitamium iodide;

mequitazin; minocromil, mizolastine; MK-886; moxastine; moxilubant; nedocromil; nedocromil calcium; nedocromil sodium; nivimedone; noberastine; norastemizole; octastine; ONO-4057; ontazolast; oxatomide; pemirolast; pentigetide; perastine; piclopastine; picumast; pirquinozol; poisonoak extract; probicromil; proxicromil; quazolast; quifenadine; quinotolast; raxofelast; repirinast; REV-5901-A; rocastine; rupatadine; SKF-S-106203; sequifenadine; setastine; sudexanox; tagorizine; talastine; tazanolast; tazifylline; temelastine; terfenadine; tetrazolast; texacromil; thiazinamium chloride; tiacrilast; tiprinast meglumine; tixanox; tranilast; WY-50295; ZD-3523; zepastine.

Amebicides:

1B-bisamidine; berythromycin; bialamicol; carbarsone; chloroquine; chloroquine; clamoxyquin; clioquinol; dehydroemetine; difetarsone; diloxanide; emetine; etofamide; Iodoquinol; lachnumon; liroldine; paromomycin sulfate; pinafide; quinfamide; satranidazole; stevaladil; stirimazole; symetine; teclozan; tetracycline; tilbroquinol;

Antiandrogens:

abiraterone; benorterone; cioteronel; cyproterone; delanterone; delmadinone; drospirenone; epitiostanol; inocoterone; L-654066; minamestane; norgestimate; osaterone; oxendolone; progesterone; rosterolone; topterone; zanoterone.

Antianemics:

ancestim; diciferron; epoetin alfa; epoetin beta; epoetin epsilon; epoetin gamma; epoetin omega; ferrous sulfate, FK-352; folic acid; gleptoferron; glutathione monoisopropyl ester; leucovorin calcium; tucaresol; TYB-5220; velaresol;

Antianginals:

alinidine; amiodarone; amlodipine besylate; amlodipine maleate; azaclorzine; barnidipine; bertosamil; betaxolol; bertosamil; bevantolol; bimakalim; butoprozine; carvedilol; CD-832; CERM-11956; cinepazet maleate; crobenetine; cyclovirubuxine-D; desocriptine; diproteverine; dopropidil; elgodipine; EMD-57283; eniporide; ethacizine; fantofarone; FK-409; flestolol; flosatidil; flosequinan; FR-46171; GP-1-468; GP-1-531; hyperin; ipramidil; isosorbide dinitrate; ivabradine; KC-764; KRN-2391; KW-3635; ligustizine; linsidomine; metoprolol succinate; mibefradil; mildronate; mivazerol; molsidomine; monatepil maleate; nafagrel; NK-341; OP-2000; pirsidomine; pivazide; pranidipine; primidolol; ranolazine; SL-87.0495; ST-1324; tedisamil; tosifen; vatanidipine; verapamil; Y-27152; zatebradine.

Anxiolytics:

adatanserin; alpidem; binospirone mesilate; bretazenil; glemanserin; ipsapirone; mirisetron maleate; ocinaplon; ondansetron; panadiplon; pancopride; pazinaclone; serazapine; tandospirone citrate; zalospirone.

Antiarthritics:

AI-200; auranofin; aurothioglucose; cipemastat; etanercept; etebenecid; interleukin-6; leflunomide; lenercept; lobenzarit; lodelaben: M-5010; parecoxib; rofecoxib; RS-130830; S-2474; TSA-234; valdecoxib;

Antiatherosclerotics:

H-327/86; mifobate; lodazecar; riboflavin butyrate; timefurone.

Bacteriostatics:

acedapsone; acetosulfone sodium; alamecin; alexidine; amdinocillin; amdinocillin pivoxil; amicycline; amifloxacin; amifloxacin mesilate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; aziocillin sodium; bacampicillin hydrochloride; bacitracin; bacitracin methylene disalicylate; bacitracin zinc; bambermycins; benzoylpas calcium; berythromycin; betamicin sulfate; blapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime; cefetecol; cefixime; cefmenoxime; cefmetazole; cefmetazole sodium; cefonicid monosodium; cefonicid sodium; cefoperazone sodium; ceforanide; cefotaxime sodium; cefotetan; cefotetan disodium; cefotiam; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin; cephaloglycin; cephaloridine; cephalothin sodium; cephapirin sodium; cephradine; cetocycline; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline; cinoxacin; ciprofloxacin; ciprofloxacin; cirolemycin; clarithromycin; clinafloxacin; clindamycin; clindamycin; clindamycin palmitate; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline; demecycline; denofungin; dlaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline; erythromycin; erythromycin acistrate; erythromycin estolate; erythromycin ethylsuccinate; erythromycin gluceptate; erythromycin lactobionate; erythromycin propionate; erythromycin stearate; ethambutol; ethionamide; fleroxacin; floxacillin; fludalanine; flumequine; fosfomycin; fosfomycin trometamine; fumoxicillin; furazolium chloride; furazolium tartrate; fusidate sodium; fusidic acid; gentamicin sulfate; gloximonam; gramicidin; haloprogin; hetacillin; hetacillin; hexedine; ibafloxacin; imipenem; isoconazole; isepamicin; isoniazid; josamycin; kanamycin sulfate; kitasamycin; levofuraltadone; levopropylcillin; lexithromycin; lincomycin; lincomycin; lomefloxacin; lomefloxacin; lomefloxacin mesilate; loracarbef; mafenide; meclocycline; meclocycline sulfosalicylate; megalomicin phosphate; mequidox; meropenem; methacycline; methacycline; methenamine; methenamine hippurate; methenamine mandelate; methicillin sodium; metioprim; metronidazole; metronidazole phosphate; mezlocillin; mezlocillin sodium; minocycline; minocycline; mirincamycin; monensin; monensin sodium; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin sodium; oximonam; oximonam sodium; oxolinic acid; oxytetracycline; oxytetracycline calcium; oxytetracycline; paldimycin; parachlorophenol; paulomycin; pefloxacin; pefloxacin mesilate; penamecillin; penicillin G benzathine; penicillin G; penicillin G procaine; penicillin G sodium; penicillin V; penicillin V benzathine; penicillin V hydrabamine; penicillin V; pentizidone sodium; phenyl aminosalicylate; piperacillin sodium; pirbenicillin sodium; piridicillin sodium; pirimycin; pivampicillin; pivampicillin pamoate; pivampicillin probenate; polymyxin B sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin; spiramycin; stallimycin; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter, sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin; telcoplanin; temafloxacin; temocillin; tetracycline; tetracycline; tetracycline phosphate complex; tetroxoprim; thiamphenicol; thiphencillin; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin; virginiamycin; zorbamycin.

Anticholinergics:

alverine citrate; anisotropine methylbromide; atropine; atropine oxide; atropine sulfate; belladonna; benapryzine; benzetimide; benzilonium bromide; biperiden; biperiden; biperiden lactate; clidinium bromide; cyclopentolate; dexetimide; dicyclomine; dihexyverine; domazoline fumarate; elantrine; elucaine; ethybenztropine; eucatropine; glycopyrrolate; heteronium bromide; homatropine hydrobromide; homatropine methylbromide; hyoscyamine; hyoscyamine hydrobromide; hyoscyamine sulfate; isopropamide iodide; mepenzolate bromide; methylatropine nitrate; metoquizine; oxybutynin chloride; parapenzolate bromide; pentapiperium methylsulfate; phencarbamide; poldine methylsulfate; proglumide; propantheline bromide; propenzolate; scopolamine hydrobromide; tematropium methylsulfate; tiquinamide; tofenacin; toquizine; triampyzine sulfate; trihexyphenidyl; tropicamide.

Anticoagulants:

ancrod; ardeparin sodium; bivalirudin; bromindione; dalteparin sodium; desirudin; dicumnarol; heparin calcium; heparin sodium; lyapolate sodium; nafamostat mesilate; phenprocoumon; tinzaparin sodium; warfarin sodium.

Anticonvulsants:

albutoin; ameltolide; atolide; buramate; carbamazepine; cinromide; citenamide; clonazepam; cyheptamide; dezinamide; dimethadione; divalproex sodium; eterobarb; ethosuximide; ethotoin; flurazepam; fluzinamide; fosphenytoin sodium; gabapentin; ilepcimide; lamotrigine; magnesium sulfate; mephenytoin; mephobarbital; methetoin; methsuximide; milacemide; nabazenil; nafimidone; nitrazepam; phenacemide; phenobarbital; phenobarbital sodium; phensuximide; phenytoin; phenytoin sodium; primidone; progabide; ralitoline; remacemide; ropizine; sabeluzole; stiripentol; sulthiame; thiopental sodium; tiletamine; topiramate; trimethadione; valproate sodium; valproic acid; vigabatrin; zoniclezole; zonisamide.

Antidepressants:

adatanserin; adinazolam; adinazolam mesilate; alaproclate; aletamine; amedalin; amitriptyline; amoxapine; aptazapine maleate; azaloxan fumarate; azepindole; azipramine; bipenamol; bupropion; butacetin; butriptyline; caroxazone; cartazolate; ciclazindol; cidoxepin; cilobamine mesilate; clodazon; clomipramine; cotinine fumarate; cyclindole; cypenamine; cyprolidol; cyproximide; daledalin tosylate; dapoxetine; dazadrol maleate; dazepinil; desipramine; dexamisole; deximafen; dibenzepin; dioxadrol; dothiepin; doxepin; duloxetine; eclanamine maleate; encyprate; etoperidone; fantridone; fehmetozole; fenmetramide; fezolamine fumarate; fluotracen; fluoxetine; fluoxetine; fluparoxan; gamfexine; guanoxyfen sulfate; imafen; imiloxan; imipramine; indeloxazine; intriptyline; iprindole; isocarboxazid; ketipramine fumarate; lofepramine; lortalamine; maprotiline; maprotiline; melitracen; milacemide; minaprine; mirtazapine; moclobemide; modaline sulfate; napactadine; napamezole; nefazodone; nisoxetine; nitrafudam; nomifensine maleate; nortriptyline; octriptyline phosphate; opipramol; oxaprotiline; oxypertine; paroxetine; pheneizine sulfate; pirandamine; pizotyline; pridefine; prolintane; protriptyline; quipazine maleate; rolicyprine; seproxetine; sertraline; sibutramine; sulpiride; suritozole; tametraline; tampramine fumarate; tandamine; thiazesim; thozalinone; tomoxetine; trazodone; trebenzomine; trimipramine; trimipramine maleate; venlafaxine; viloxazine; zimeldine; zometapine.

Antidiabetics:

acetohexamide; bimoclomol; BM-17.0249; buformin; butoxamine; carbutamide; centpiperalone; chlorpropamide; clomoxir; etoformin; etomoxir; fenbutamide; GI-262570; gliamilide; glibenclamide; glibornuride; glibutimine; glicaramide; glicetanile sodium; gliciazide; glicondamide; glidazamide; gilflumide; glimepiride; glipalamide; glipizide; gliquidone; glisamuride; glisentide; glisindamide; glisolamide; glisoxepide; glucagon; glyburide; glybuthiazol; glybuzole; glyclopyramide; glycyclamide; glyhexamide; glymidine sodium; glyoctamide; glyparamide; glypinamide; glyprothiazol; glysobuzole; heptolamide; HMR-1964; insulin; insulin argine; insulin aspart; insulin dalanat; insulin defalan; insulin detemir; insulin glargine; insulin human; insulin human, isophane; insulin human zinc; insulin human zinc, extended; insulin, isophane; insulin lispro; insulin, neutral; insulin zinc; insulin zinc, extended; insulin zinc; isaglidole; JTT-501; JTT-608; mebenformin; metahexamide; metformin; methyl palmoxirate; metyrapone; midaglizole; mitiglinide; nateglinide; NN-304; NVP-DPP-728; palmoxirate sodium; PNU-106817; pramlintide; proinsulin human; seglitide acetate; tibeglisene; tiformin; tolazamide; tolbutamide; tolpyrramide;

Aldose Reductase Inhibitors:

AD-5467; alrestatin; ciglitazone; darglitazone; englitazone sodium; epairestat; fidarestat; imirestat; linogliride; linogliride; MCC-555; minalrestat; NZ-314; pioglitazone; pirogliride; ponalrestat; sorbinil; risarestat; rosiglitazone; tendamistat; tolrestat; troglitazone; zenarestat; zopolrestat.

Alpha-Glucosidase Inhibitors:

acarbose; camiglibose; emiglitate; englitazone; miglitol; moranoline; voglibose.

Antidiarrheals:

rolgamidine, diphenoxylate (Lomotil), metronidazole (Flagyl), methylprednisolone (Medrol), sulfasalazine (Azulfidine).

Antidiuretics:
argipressin tannate; desmopressin acetate; lypressin.

Antidotes:
dimercaprol; edrophonium chloride; fomepizole; leucovorin calcium; levoleucovorin calcium; methylene blue; protamine sulfate.

Antiemetics:
alosetron; batanopride; bemesetron; benzquinamide; chlorpromazine; chlorpromazine; clebopride; cyclizine; dimenhydrinate; diphenidol; diphenidol; diphenidol pamoate; dolasetron mesilate; domperidone; dronabinol; fludorex; flumeridone; galdansetron; granisetron; granisetron; lurosetron mesilate; meclizine; metoclopramide; metopimazine; ondansetron; pancopride; prochlorperazine; prochlorperazine edisylate; prochlorperazine maleate; promethazine; thiethylperazine; thiethylperazine malate; thiethylperazine maleate; trimethobenzamide; zacopride.

Antiepileptics:
felbamate; loreclezole; tolgabide.

Antiestrogens (Non-Steroidal):
clometherone; delmadinone acetate; nafoxidine; nitromifene citrate; raloxifene; tamoxifen citrate; toremifene citrate; trioxifene mesilate.

Antifibrinolytics:
camostat; nafamostat mesilate.

Fungistatics:
acrisorcin; ambruticin; amphotericin B; azaconazole; azaserine; basifungin; bifonazole; biphenamine; bispyrithione magsulfex; butoconazole nitrate; calcium undecylenate; candicidin; carbol-fuchsin; chlordantoin; ciclopirox; ciclopirox olamine; cilofungin; cisconazole; clotrimazole; cuprimyxin; denofungin; dipyrithione; doconazole; econazole; econazole nitrate; enilconazole; ethonam nitrate; fenticonazole nitrate; filipin; fluconazole; flucytosine; fungimycin; griseofulvin; hamycin; isoconazole; itraconazole; kalafungin; ketoconazole; lomofimgin; lydimycin; mepartricin; miconazole; miconazole nitrate; monensin; monensin sodium; naftifine; neomycin undecylenate; nifuratel; nifurmerone; nitralamine; nystatin; octanoic acid; orconazole nitrate; oxiconazole nitrate; oxifungin; parconazole; partricin; iodide; proclonol; pyrithione zinc; pyrrolnitrin; rutamycin; sangulnarium chloride; saperconazole; scopafungin; selenium sulfide; sinefungin; sulconazole nitrate; terbinafine; terconazole; thiram; ticlatone; tioconazole; tolciclate; tolindate; tolnaftate; triacetin; triafungin; undecylenic acid; viridofulvin; zinc undecylenate; zinoconazole.

Glaucoma Drugs:
alprenoxime; colforsin; dapiprazole; dipivefrin; naboctate; pilocarpine; pimabine.

Antihistamines:
acrivastine; antazoline phosphate; astemizole; azatadine maleate; barmastine; bromodiphenhydramine; brompheniramnine maleate; carbinoxamine maleate; cetirizine; chlorpheniramine maleate; chlorpheniramine polistirex; cinnarizine; clemastine; clemastine fumarate; closiramine aceturate; cycliramine maleate; cyclizine; cyproheptadine; dexbrompheniramnine maleate; dexchlorpheniramine maleate; dimethindene maleate; diphenhydramine citrate; diphenhydramnine; dorastine; doxylamine succinate; ebastine; levocabastine; loratadine; mianserin; noberastine; orphenadrine citrate; pyrabrom; pyrilamine maleate; pyroxamnine maleate; rocastine; rotoxamine; tazifylline; temelastine; terfenadine; tripelennamine citrate; tripelennamine; triprolidine; zolamine.

Lipid-Lowering Agents:
cholestyramine resin; clofibrate; colestipol; crilvastatin; dalvastatin; dextrothyroxine sodium; fluvastatin sodium; gemfibrozil; lecimibide; lovastatin; niacin; pravastatin sodium; probucol; simvastatin; tiqueside; xenbucin; acifran; beloxamide; bezafibrate; boxidine; butoxamine; cetaben sodium; ciprofibrate; gemcadiol; halofenate; lifibrate; meglutol; nafenopin; pimetine; theofibrate; tibric acid; treloxinate.

Antihypertensives:
alfuzosin; alipamide; althiazide; amiquinsin; amiodipine besylate; amiodipine maleate; anaritide acetate; atiprosin maleate; belfosdil; bemitradine; bendacalol mesilate; bendroflumethiazide; benzthiazide; betaxolol; bethanidine sulfate; bevantolol; biclodil; bisoprolol; bisoprolol fumarate; bucindolol; bupicomide; buthiazide: candoxatril; candoxatrilat; captopril; carvedilol; ceronapril; chlorothiazide sodium; cicletanine; cilazapril; clonidine; clonidine; clopamide; cyclopenthiazide; cyclothiazide; darodipine; debrisoquin sulfate; delapril; diapamide; diazoxide; dilevalol; diltiazem malate; ditekiren; doxazosin mesilate; ecadotril; enalapril maleate; enalaprilat; enalkiren; endralazine mesilate; epithiazide; eprosartan; eprosartan mesilate; fenoldopam mesilate; flavodilol maleate; flordipine; flosequinan; fosinopril sodium; fosinoprilat; guanabenz; guanabenz acetate; guanacline sulfate; guanadrel sulfate; guancydine; guanethidine monosulfate; guanethidine sulfate; guanfacine; guanisoquin sulfate; guanoclor sulfate; guanoctine; guanoxabenz; guanoxan sulfate; guanoxyfen sulfate; hydralazine; hydralazine polistirex; hydroflumethiazide; indacrinone; indapamide; indolaprif; indoramin; indoramin; indorenate; lacidipine; leniquinsin; levcromakalim; lisinopril; lofexidine; losartan; losulazine; mebutamate; mecamylamine; medroxalol; medroxalol; methalthiazide; methyclothiazide; methyldopa; methyldopate; metipranolol; metolazone; metoprolol fumarate; metoprolol succinate; metyrosine; minoxidil; monatepil maleate; muzolimine; nebivolol; nitrendipine; ofornine; pargyline; pazoxide; pelanserin; perindopril erbumine; phenoxybenzamine; pinacidil; pivopril; polythiazide; prazosin; primidolol; prizidilol; quinapril; quinaprilat; quinazosin; quinelorane; quinpirole; quinuclium bromide; ramipril; rauwolfia serpentina; reserpine; saprisartan; saralasin acetate; sodium nitroprusside; sulfinalol; tasosartan; teludipine; temocapril; terazosin; terlakiren; tiamenidine; tiamenidine; ticrynafen; tinabinol; tiodazosin; tipentosin; trichlormethiazide; trimazosin; trimethaphan camsylate; trimoxamine; tripamide; xipamide; zankiren; zofenoprilat arginine.

Antihypotensives:
ciclafrine; midodrine.

Antiinflammatory Agents:
alclofenac; alclometasone dipropionate; algestone acetonide; alpha amylase; amcinafal; amcinafide; amfenac sodium; amiprilose; anakinra; anirolac; anitrazafen; apazone; balsalazide disodium; bendazac; benoxaprofen; benzydamine; bromelains; broperamole; budesonide; carprofen; ciclofren; cintazone; cliprofen; clobetasol proplonate; clobetasone butyrate; clopirac; cloticasone proplonate; cormethasone acetate; cortodoxone; deflazacort; desonide; desoximetasone; dexamethasone dipropionate; diclofenac; diclofenac sodium; diflorasone diacetate; diflumidone sodium; diflunisal; difluprednate; diftalone; dimethyl sulfoxide; drocinonide; endrysone; enlimomab; enolicam sodium; epirizole; etodolac; etofenamate; felbinac; fenamole; fenbufen; fenclofenac; fenclorac; fendosal; fenpipalone; fentiazac; flazalone; fluazacort; flufenamic acid; flumizole; flunisolide acetate; flunixin; flunixin meglumine; fluocortin butyl; fluorometholone acetate; fluquazone; flurbiprofen; fluretofen; fluticasone propionate; furaprofen; furobufen; halcinonide; halobetasol propionate; halopredone acetate; ibufenac; ibuprofen; ibuprofen aluminum; ibuprofen piconol; ilonidap; indomethacin; indomethacin sodium; indoprofen;

indoxole; intrazole; isoflupredone acetate; isoxepac; isoxicam; ketoprofen; lofemizole; lornoxicam; lonazolac; loteprednol etabonate; meclofenamate sodium; meclofenamic acid; meclorisone dibutyrate; mefenamic acid; mesalamine; meseclazone; methylprednisolone suleptanate; momiflumate; nabumetone; naproxen; naproxen sodium; naproxol; nimazone; olsalazine sodium; orgotein; orpanoxin; oxaprozin; oxyphenbutazone; paranyline; pentosan polysulfate sodium; phenbutazone sodium glycerate; pirfenidone; piroxicam; piroxicam cinnamate; piroxicam olamine; pirprofen; prednazate; prifelone; prodolic acid; proquazone; proxazole; proxazole citrate; rimexolone; romazarit; salcolex; salnacedin; salsalate; sanguinarium chloride; seclazone; sermetacin; sudoxicam; sulindac; suprofen; talmetacin; talniflumate; talosalate; tebufelone; tenidap; tenidap sodium; tenoxicam; tesicam; tesimide; tetrydamine; tiopinac; tixocortol pivalate; tolmetin; tolmetin sodium; triclonide; triflumidate; zidometacin; zomepirac sodium.

Antimalarials:

acedapsone; amodiaquine; amquinate; arteflene; chloroquine; chloroquine; chloroquine phosphate; cycloguanil pamoate; enpiroline phosphate; halofantrine; hydroxychloroquine sulfate; mefloquine; menoctone; mirincamycin; primaquine phosphate; pyrimethamine; quinine sulfate; tebuquine.

Microbicides:

aztreonam; chlorhexidine gluconate; imidurea; lycetamine; nibroxane; pirazmonam sodium; propionic acid; pyrithione sodium; sanguinarium chloride; tigemonam dicholine.

Antimigraine Agents:

almotriptan; alniditan; avitriptan; azasetron; azatadine; bemesetron; BIBN-4096BS; BMS-181885; bromocriptine; dolasetron; donitriptan; ebalzotan; eletriptan; ergotamine; frovatriptan; lprazochrome; IS-159; lisuride; lomerizine; LY-334370; LY-53857; metergoline; metergotamine; methysergide; naratriptan; ORG-GC-94; oxetorone; pipethiadene; pizotifen; propisergide; rizatriptan; sergolexole; sumatriptan; tropanserin; tropoxin; UK-116044; valofane; zatosetron; zolmitriptan.

Active Ingredients for Sea Sickness and Vomiting:

buclizine; cyclizine lactate; naboctate.

Cytostatics:

acivicin; aclarubicin; acodazole; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene; bisnafide dimesilate; bizelesin; bleomycin sulfate; brequinar sodium; bropirimine; busulfan; cactinomycin; calusterone; caracemide; carbetimer; carboplatin; carmustine; carubicin; carzelesin; cedefingol; chlorambucil; cirolemycin; cisplatin; cladribine; crisnatol mesilate; cyclophosphamide; cytarabine; dacarbazine; dactinomycin; daunorubicin; decitabine; dexormaplatin; dezaguanine; dezaguanine mesilate; diaziquone; docetaxel; doxorubicin; doxorubicin; droloxifene; droloxifene citrate; dromostanolone propionate; duazomycin; edatrexate; eflornithine; elsamitrucin; enloplatin; enpromate; epipropidine; epirubicin; erbulozole; esorubicin; estramustine; estramustine phosphate sodium; etanidazole; ethiodized oil I 131; etoposide; etoposide phosphate; etoprine; fadrozole; fazarabine; fenretinide; floxuridine; fludarabine phosphate; fluorouracil; flurocitabine; fosquidone; fostriecin sodium; gemcitabine; gemcitabine; gold Au 198; hydroxyurea; idarubicin; ifosfamide; ilmofosine; interferon alfa-2a; interferon alfa-2b; interferon alfa-n1; interferon alfa-n3; interferon beta-I a; interferon gamma-I b; iproplatin; irinotecan; lanreotide acetate; letrozole; leuprolide acetate; liarozole; lometrexol sodium; lomustine; losoxantrone; masoprocol; maytansine; mechlorethamine; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone; plicamycin; plomestane; porfimer sodium; porfiromycin; prednimustine; procarbazine; puromycin; puromycin; pyrazofurin; riboprine; rogletimide; safmgol; safingol; semustine; simtrazene; sparfosate sodium; sparsomycin; spirogermanium; spiromustine; spiroplatin; streptonigrin; streptozocin; strontium chloride Sr 89; sulofenur; talisomycin; taxane; taxoid; tecogalan sodium; tegafur; teloxantrone; temoporfin; teniposide; teroxirone; testolactone; thiamiprine; thioguanine; thiotepa; tiazofurin; tirapazamine; topotecan; toremifene citrate; trestolone acetate; triciribine phosphate; trimetrexate; trimetrexate glucuronate; triptorelin; tubulozole; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin.

Active Ingredient for Combination Therapy with Cytostatics:

imipramine and desipramine.

Antiparkinson Agents:

benztropine mesilate; biperiden; biperiden; biperiden lactate; carmantadine; ciladopa; dopamantine; ethopropazine; lazabemide; levodopa; lometraline; mofegiline; naxagolide; pareptide sulfate; procyclidine; quinetorane; ropinirole; selegiline; tolcapone; trihexyphenidyl, antiperistaltic: difenoximide; difenoxin; diphenoxylate; fluperamide; lidamidine; loperamide; malethamer; nufenoxole; paregoric.

Antiproliferative Active Ingredients:

piritrexim isethionate.

Antiprotozoal Active Ingredients:

amodiaquine; azanidazole; bamnidazole; carnidazole; chlortetracycline bisulfate; chlortetracycline; flubendazole; flunidazole; halofuginone hydrobromide; imidocarb; ipronidazole; metronidazole; misonidazole; moxnidazole; nitarsone; partricin; puromycin; puromycin; ronidazole; sulnidazole; tinidazole.

Active Ingredients for Treating Pruritus:

cyproheptadine; methdilazine; methdilazine; trimeprazine tartrate.

Psoriasis Active Ingredients:

acitretin; anthralin; azaribine; calcipotriene; cycloheximide; enazadrem phosphate; etretinate; liarozole fumarate; lonapalene; tepoxalin.

Neuroleptics:

acetophenazine maleate; alentemol hydrobromide; alpertine; azaperone; batelapine maleate; benperidol; benzindopyrine; brofbxine; bromperidol; bromperidol decanoate; butaclamol; butaperazine; butaperazine maleate; carphenazine maleate; carvotroline; chlorpromazine; chlorpromazine; chlorprothixene; cinperene; cintriamide; clomacran phosphate; clopenthixol; clopimozide; clopipazan mesilate; cloroperone; clothiapine; clothixamide maleate; clozapine; cyclophenazine; droperidol; etazolate; fenimide; flucindole; flumezapine; fluphenazine decanoate; fluphenazine enanthate; fluphenazine; fluspiperone; fluspirilene; flutroline; gevotroline; halopemide; haloperidol; haloperidol decanoate;

iloperidone; imidoline; lenperone; mazapertine succinate; mesoridazine; mesoridazine besylate; metiapine; milenperone; milipertine; molindone; naranol; neflumozide; ocaperidone; olanzapine; oxiperomide; penfluridol; pentiapine maleate; perphenazine; pimozide; pinoxepin; pipamperone; piperacetazine; pipotiazine palniitate; piquindone; prochlorperazine edisylate; prochlorperazine maleate; promazine; remoxipride; remoxipride; rimcazole; seperidol; sertindole; setoperone; spiperone; thioridazine; thioridazine; thiothixene; thiothixene; tioperidone; tiospirone; trifluoperazine; trifluperidol; triflupromazine; triflupromazine; ziprasidone.

Antirheumatics:
auranofin; aurothioglucose; bindarit; lobenzarit sodium; phenylbutazone; pirazolac; prinomide tromethamine; seprilose.

Antischistosomal Agents:
becanthone; hycanthone; lucanthone; niridazole; oxamniquine; pararosaniline pamoate; teroxalene.

Active Ingredients for Treating Seborrhea:
chloroxine; piroctone; piroctone olamine; resorcinol monoacetate.

Antispasmolytics:
stilonium iodide; tizanidine.

Antithrombotics:
argatroban; anagrelide; bivalirudin; dalteparin sodium; domitroban; daltroban; danaparoid sodium; dazoxiben; E-3040; efegatran sulfate; enoxaparin sodium; ifetroban; ifetroban sodium; KW-3635; LCB-2853; linotroban; mipitroban; NM-702; picotamide; ramatroban; ridogrel; S-1452; samixogrel; seratrodast; sulotroban; terbogrel; tinzaparin sodium; trifenagrel.

Antitussives:
benproperine; benzonatate; bibenzonium bromide; bromhexine; butamirate citrate; butetamate; clobutinol; chlofedanol; codeine; codeine polistirex; codoxime; dextromethorphan; dextromethorphan polistirex; dihydrocodeine; dimethoxanate; dropropizine; drotebanol; eprazinone; ethyl dibunate; fedrilate; guaiapate; hydrocodone; hydrocodone polistirex; iquindamine; isoaminile; levdropropizine; levopropoxyphene napsylate; medazomide; meprotixol; moguisteine; morclofone; nepinalone; noscapine; pemerid nitrate; pentoxyverine; pholcodine; picoperine; pipazetate; prenoxdiazine; promolate; saredutant; sodium dibunate; suxemerid sulfate; thebacon; tipepidine; vadocaine; zipeprol.

Antiulcer Agents:
histamine H2 antagonists
BL-6271; BL-6341A; BMY-25368; BRL-28390; cimetidine; dalcotidine; donetidine; ebrotidine; etintidine; famotidine; ICI-162846; icotidine; IGN-2098; isotiquimide; lafutidine; lamtidine; lavoltidine; lupitidine; mifentidine; niperotidine; nizatidine; osutidine; oxmetidine; pibutidine; pifatidine; ramixotidine; ranitidine; ranitidine bismuth citrate; ranitidine nitrate; roxatidine; sufotidine; TAS; tiotidine; venritidine; WHR-2348; YM-14471; zaltidine; zolantidine.

Proton Pump Inhibitors
disuprazole; esomeprazole; FPL-65372-XX; H-335/25; H-405/02; HN-11203; IY-81149; lansoprazole; leminoprazole; lucartamide; N-2220; NC-1300; nepaprazole; omeprazole; pantoprazole; pantoprazole sodium; picartamide; picoprazole; pumaprazole; rabeprazole; saviprazole; SCH-28080; SKF-95-601; SKF-96067; SKF-97574; T-330; T-776; tenatoprazole; ufiprazole; YH-1885; YM-19020.

Prostaglandins
arbaprostil; butaprost; deprostil; dimethyldinoprostone; dimoxaprost; enisoprost; enprostil; mexiprostil; misoprostol; nocloprost; ornoprostil; oxoprostol; remiprostol; rioprostil; rosaprostol; SC-30249; spiriprostil; TEI-1226; tiprostanide; trimoprostil;

Other Antiulcer Agents
aceglutamide aluminium; AD-1308; benexate; benzotript; beperidium iodide; bifemelane; BTM-1086; cadexomer iodine; cetraxate; CF-19415; CHINOIN-127; darenzepine; deboxamet; detralfate; DH-6615; dosmalfate; ecabapide; ecabet; esaprazole; espatropate; gefarnate; irsogladine; KW-5805; lactalfate; lozilurea; MAR-99; MCI-727; MDL-201034; mezolidon; molfarnate; nolinium bromide; nuvenzepine; octreotide; P-1100; pifarnine; pirenzepine; plaunotol; polaprezinc; rebamipide; RGH-2961; rispenzepine; rotraxate; setiptiline; siltenzepine; sofalcone; sucralfate; sucrosofate; sulglicotide; telenzepine; teniloxazine; teprenone; tiopropamine; tolimidone; triletide; tritlozine; troxipide; UH-AH-37; zolenzepine; zolimidine.

Agents for Treating Urolithiasis:
benzoic acid; cysteamine; cysteamine; tricitrates.

Virustatic Agents:
abacavir; acemannan; aciclovir; adefovir; alovudine; alvircept sudotox; atevirdine; amantadine; aranotin; arildone; atevirdine; avridine; BW-935-U83; calanolide B; cidofovir; cipamfylline; cytarabine; DAPD; delavirdine; desciclovir; didanosine; disoxaril; DPC-083; edoxudine; efavirenz; emivirine; enviradene; enviroxime; famciclovir; famotine; fiacitabine; fialuridine; fosarilate; foscarnet sodium; fosfonet sodium; ganciclovir; GW-420867X; idoxuridine; kethoxal; L-697661; lamivudine; lobucavir; memotine; methisazone; nevirapine; NSC-678323; penciclovir; pirodavir; ribavirin; rimantadine; S-1153; saquinavir; somantadine; sorivudine; statolon; stavudine; talviraline; thioctic acid; tilorone; trifluridine; trovirdine; U-93923; valaciclovir; vidarabine; vidarabine; vidarabine; viroxime; zalcitabine; zidovudine; zinviroxime.

Active Ingredients for Treating Benign Prostate Hyperplasia:
alfuzosin; CEP-701; doxazosin; dutasteride; FK-143; GI-231818; GYKI-16084; levormeloxifene; pirfenidone; RS-97078; tamsulosin; sitoglusid.

Active Ingredients for Treating Osteoporosis:
alendronic acid; butedronic acid; clodronic acid; EB-1053; etidronic acid; ibandronic acid; incadronic acid; medronic acid; minodronic acid; neridronic acid; olpadronic acid; oxidronic acid; pamidronic acid; piridronic acid; ranelic acid; risedronic acid; tiludronic acid; YM-529; zoledronic acid.

Carbonic Anhydrase Inhibitors:
acetazolamide; AL-4414A; diclofenamide; dorzolamide; methazolamide; sezolamide; sulocarbilate.

Antiarrhythmics:
abanoquil; ACC-9164; acecainide; actisomide; adenosine; ajmaline; alinidine; almokalant; alprafenone; amafolone; ambasilide; ameltolide; amiodarone; aprindine; aprindine; artilide; asocainol; AWD-G-256; azimilide; benderizine; benrixate; benzodioxine; berlafenone; bertosamil; bidisomide; bisaramil; BRL-32642; bucainide; bucromarone; bunaftine; buquineran; butobendine; butoprozine; capobenic acid; carbizocaine; carcainium chloride; cariporide; carocainide; cercainide; cibenzoline; cifenline; ciprafamide; CL-284027; clamikalant; clofilium phosphate; CV-6402; CVT-510; cyclovirobuxine-D, D-230; detajmium bitartrate; disobutamide; dexsotalol; dioxadilol; diprafenone; disobutamide; disopyramide; dofetilide; drobuline; dronedarone; droxicainide; E047/1; E-0747; E-4031; edifolone; emilium tosilate; emopamil; encainide; eproxindine; erocainide; ersentilide; fepromide; flecainide; fluzoperide; gallanilide; glemanserin; guafecainol; GYKI-23107; GYKI-38233; heptacaine; hydroxyfenone; ibutilide; indecainide; ipazilide; itrocainide; ketocainol; L-702958; L-706000; levosemotiadil; lorajmine; lorcainide; meobentine; mexiletine; milacainide; modecainide; moracizine; moxaprindine; murocainide; nibentan; nicainoprol; nipekalant; nofecainide; oxiramide; palatrigine; penticainide; pentisomide; pilsicainide; pirmenol; pirolazamide; prajmalium bitartrate; pranolium chloride; prifuroline; procainamide; propafenone; pyrinoline; quinacainol; quindonium bromide; quinidine; recainam; rilozarone; risotilide; ronipamil; ropitoin; sematilide; sinomenine; solpecainol; sparteine; stirocainide; stobadine; SR-47063; sulamserod; suricainide; tedisamil; terikalant; tiracizine; tocainide; tosifen; transcainide; trecetilide; zocainone.

Cardiotonics:

acadesine; acetyldigitoxin; acetyldigoxin; acrihellin; actodigin; adibendan; amrinone; amselamine; arbutamine; arpromidine; AWD-122-239; bemoradan; bucladesine; butopamine; carbazeran; cariporide; carperitide; carsatrin; CGS-13928C; cilobradine; CK-2130; CK-2289; colforsin; CV-6402; denopamine; deslanoside; dexrazoxane; digitalis; digitoxin; digoxin; dobutamine; dobutamine; docarpamine; domipizone; dopexamine; doridosine; doxaminol; DPI-201-106; draflazine; eniporide; enoximone; ER-21355; evodiamine; falipamil; FK-664; fosfructose; FR-113453; FR-46171; gapromidine; gitaloxin; gitoformate; JP-1-468; GP-1-531; GP-668; heptaminol; higenamine; ibopamine; imazodan; indolidan; isamoltan; isomazole; levacecamine; levdobutamine; levosimendan; limaprost; linsidomine; lixazinone; MCI-154; medorinone; meproscillarin; meribendan; metildigoxin; mildronate; milrinone; mioflazine; mixidine; MS-857; nanterinone; neraminol; NKH-477; olprinone; OPC-18750; otenzepad; oxfenicine; pelrinone; pengitoxin; pentrinitrol; peruvosid; pimobendan; pioximone; pirsidomine; prinoxodan; prisotinol; propionylcarnitine; proscillaridin; quazinone; quazodine; quindonium bromide; ramnodigin; revizinone; saterinone; siguazodan; simendan; sulmazole; thevetosid; toborinone; ubidecarenone; vesnarinone; VPA-985.

Choleretic Agents:

alibendol; azintamide; boldine; cicloxilic acid; cinametic acid; clanobutin; dehydrocholic acid; dibuprol; epomediol; exiproben; febuprol; fencibutirol; fenipentol; hexacyprone; hymecromone; menbutone; moquizone; piprozolin; prazapine; sincalide; tenylidone; terbuprol; tocamphyl; trepibutone.

Cholinergic Agents:

aceclidine; bethanechol chloride; carbachol; demecarium bromide; dexpanthenol; echothiophate iodide; isoflurophate; methacholine chloride; neostigmine bromide; neostigmine methylsulfate; physostigmine; physostigmine salicylate; physostigmine sulfate; pilocarpine; pilocarpine; pilocarpine nitrate; pyridostigmine bromide.

Cholinergic Agonists:

xanomeline; xanomeline tartrate.

Cholinesterase Inhibitors:

acetohydroxamic acid; DMPS; amiphenazole; obidoxime chloride; pralidoxime chloride; pralidoxime iodide; pralidoxime mesilate.

Coccidiostats:

aklomide; amidapsone; amprolium; arprinocid; bitipazone; buquinolate; ciadox; clazuril; clopidol; decoquinate; diclazuril; dinitolamide; dinsed; halofuginone; letrazuril; narasin; nequinate; nicarbazine; nifursemizone; ponazuril; proquinolate; robenidine; semduramicin; sulazuril; sulfanitran; tiazuril; tosulur.

Diuretics:

acetazolamide; acetothiazide; alipamide; altizide; amanozine; ambuphylline; ambuside; amiloride; aminometradine; amisometradine; ampyrimine; apaxifylline; azolimine; azosemide; bemetizide; bemitradine; bendroflumethiazide; benzamil; benzolamide; benzthiazide; benzylhydrochlorothiazide; besulpamide; besunide, brocrinat; bumetanide; butizide; canrenoic acid; carmetizide; chlorazanil; chlorothiazide; chlorthalidone; cicletanine; clazolimine; clopamide; clorexolone; CVT-124; dicirenone; disulfamide; etamiphylline; ethacrynate sodium; ethacrynic acid; etofylline; etozolin; fenquizone; FK-352; FR-113453; furosemide; hydrochlorothiazide; hydroflumethiazide; indacrinone; indapamide; isosorbide; KW-3902; lemidosul; mannitol; mebutizide; mefruside; methalthiazide; methazolamide; methyclothiazide; meticrane; metolazone; muzolimine; niravoline; OPC-31260; oxprenoate; ozolinone; paraflutizide; penflutizide; piretanide; polythiazide; canrenoate; propazolamide; prorenoate; prorenone; pytamine; quincarbate; quinethazone; RPH-2823; S-8666; sitalidone; spironolactone; spirorenone; spiroxasone; SR-48692; sulciamide; sulicrinat; sulocarbilate; sulosemide; sumetizide; teclothiazide; tiamizide; tienilic acid; torsemide; triamterene; trichlormethiazide; triflocin; tripamide; TRK-820; ularitide; urea; xipamide.

Ectoparasiticides: carbaril; clidafidine; cypermethrin; eprinomectin; fenclofos; fenvalerate; ivermectin; lindane; moxidectin; nifluridide; permethrin; temefos.

Emetics:

apomorphine.

Enzyme Inhibitors:

acetohydroxamic acid; alrestatin sodium; aprotinin; benazepril; benazeprilat; benurestat; bromocriptine; bromocriptine mesilate; cilastatin sodium; flurofamide; lergotrile; lergotrile mesilate; levcycloserine; libenzapril; pentopril; pepstatin; perindopril; polignate sodium; sodium amylosulfate; sorbinil; spirapril; spiraprilat; taleranol; teprotide; tolfamide; zofenopril calcium.

Estrogens:

chlorotrianisene; dienestrol; diethylstilbestrol; diethylstilbestrol diphosphate; equilin; epimestrol; estradiol; estradiol cypionate; estradiol enanthate; estradiol undecylate; estradiol valerate; estrazinol hydrobromide; estriol; estrofurate; estrogens, conjugated; estrogens, esterified; estrone; estropipate; ethinyl estradiol; fenestrel; mestranol; nylestriol; quinestrol Fibrinolytics:

acexamic acid; amediplase; anistreplase; aprotinin; bisobrin lactate; brinase; brinolase; camostat; fibrinolysin; inicarone; iquindamine; nattokinase; pamiteplase; picotamide; staplabin; streptokinase; taurine; tizabrin; tranexamic acid;

Free-Radical Scavenger:

pegorgotein.

Motility-Increasing Active Ingredients:

cisapride (Propulsid); metoclopramide (Reglan); hyoscyamine (Levsin).

Glucocorticosteroids:

acrocinonide; alclometasone; algestone acetonide; amcinafal; amcinafide; amcinonide; amebucort; amelometasone; beclomethasone dipropionate; bendazacort; betamethasone; betamethasone acetate; betamethasone benzoate; betamethasone dipropionate; betamethasone sodium phosphate; betamethasone valerate; budesonide; butixocort; butixocort propionate; CGP-13774; ciclesonide; ciclometasone; ciprocinonide; clobetasol; clobetasol 17-propionate; clobetasone; clocortolone acetate; clocortolone pivalate; cloprednol; cloticasone; cloticasone propionate; CMJ; cormetasone; corticotropin; corticotropin; corticotropin zinc hydroxide; cortisone acetate; cortisuzol; cortivazol; deflazacort;

deprodone; deprodone propionate; descinolone acetonide; desonide; desoximetasone; desoxycortone; dexamethasone; dexamethasone acefurate; dexamethasone sodium phosphate; dexbudesonide; dichlorisone; diflorasone; diflucortolone; diflucortolone pivalate; difluprednate; dimesone; domoprednate; doxibetasol; drocinonide; FSDCICM; fluazacort; fluclorolone acetonide; flucloronide; fludrocortisone; fludroxycortide; flumetasone; flumetasone pivalate; flumoxonide; flunisolide; fluocinolone acetonide; fluocinonide; fluocortin; fluocortin butyl; fluocortolone; fluocortolone caproate; fluorometholone; flupamesone; fluperolone acetate; fluprednidene; fluprednisolone; fluprednisolone valerate; flurandrenolide; fluticasone; fluticasone propionate; formocortal; gestonorone caproate; GW-215864X; GW-250945; halcinonide; halocortolone; halometasone; halopredone acetate; hydrocortamate; hydrocortisone; hydrocortisone acetate; hydrocortisone aceponate; hydrocortisone buteprate; hydrocortisone butyrate; hydrocortisone enbutate; hydrocortisone sodium phosphate; hydrocortisone sodium succinate; hydrocortisone valerate; icometasone enbutate; isoflupredone; isoprednidene; itrocinonide; locicortolone; locicortolone dicibate; loteprednol etabonate; mazipredone; meclorisone; medrysone; meprednisone; methylprednisolone; methylprednisolone acetate; methylprednisoloxime sodium phosphate; methylprednisolone sodium succinate; mometasone furoate; naflocort; nivacortol; nivazol; paramethasone acetate; prednazate; prednazoline; prednicarbate; prednisolamate; prednisolone; prednisolone acetate; prednisolone farnesylate; prednisolone hemisuccinate; prednisolone sodium phosphate; prednisolone sodium succinate; prednisolone tebutate; prednisone; prednylidene; pregnenolone; prednival; procinonide; resocortol; rimexolone; rofleponide; TBI-PAB; ticabesone propionate; timobesone; tipredane; tixocortol; tixocortol pivalate; tralonide; triamcinolone; triamcinolone acetonide; triamcinolone acetonide sodium; triamcinolone benetonide; triamcinolone diacetate; triamcinolone furetonide; triamcinolone hexacetonide; triclonide; ulobetasol.

Hemostatics:
aminocaproic acid; oxamarin; sulmarin; thrombin; tranexamic acid.

Hormones:
diethylstilbestrol; progesterone; 17-hydroxy progesterone; medroxyprogesterone; norgestrel; norethynodrel; estradiol; megestrol (Megace); norethindrone; levonorgestrel; ethyndiol; ethinyl estradiol; mestranol; estrone; equilin; 17-alpha-dihydroequilin; equilenin; 17 alpha dihydroequilenin; 17-alpha-estradiol; 17-beta-estradiol; leuprolide (lupron); glucagon; testolactone; clomiphene; han memopausal gonadotropins; human chorionic gonadotropin; urofollitropin; bromocriptine; gonadorelin; luteinizing hormone releasing hormone and analogs; gonadotropins; danazol; testosterone; dehydroepiandrosterone; androstenedione; dihydroestosterone; relaxin; oxytocin; vasopressin; folliculostatin; follicle regulatory protein; gonadoctrinins; oocyte maturation inhibitor; insulin growth factor; follicle stimulating hormone; luteinizing hormone; tamoxifen; corticorelin ovine triftutate; cosyntropin; metogest; pituitary, posterior; seractide acetate; somalapor; somatrem; somatropin; somenopor; somidobove.

HMG-CoA Reductase Inhibitors:
lovastatin (Mevacor); simvastatin (Zocor); pravastatin (Pravachol); fluvasatin (Lescol).

Immunomodulators:
dimepranol acedoben; imiquimod; interferon beta-Ib; lisofylline; mycophenolate mofetil; prezatide copper acetate.

Immunoregulators:
azarole; fanetizole mesilate; frentizole; oxamisole; ristianol phosphate; thymopentin; tilomisole.

Immunostimulants:
loxoribine; teceleukin.

Immunosuppressants:
azathioprine; azathioprine sodium; cyclosporine; daltroban; gusperimus trihydrochloride; sirolimus; tacrolimus.

Active Ingredients for Treating Impotence:
abanoquil; alprostadil; amlodipine; BMS-193884; delequamine; doxazosin, E-4010; glycerol trinitrate; IC-351; melanotan II; minoxidil; nitraquazone; papaverine; phenoxybenzamine; prazosin; quinelorane; sildenafil; UK-114542; urapidil; vardenafil; VIP; yohimbin;

LHRH Antagonists:
deslorelin; goserelin; histrelin; lutrelin acetate; nafarelin acetate.

Hepatoprotectant:
malotilate.

Luteolytics:
fenprostalene.

Cerebrotonics:
aloracetam; alvameline; aniracetam; apaxifylline; aptiganel; azetirelin; brovincamine; cebaracetam; cevimeline; CI-844; CI-933; demiracetam; dimoxamine; donepezil; dupracetam; edaravone; ensaculin; fasoracetam; FK-960; gavestinel; igmesine; muracetam; IOS-11212; JTP-4819; KST-5410; leteprinim; ligustizine; linopirdine; MCI-225; milameline; MKC-231; NDD-094; nebracetam; nicoracetam; nizofenone; ONO-1603; OP-2507; OPC-14117; oxiracetam; pikamilone; piracetam; piraxelate; pirglutargine; pramiracetam; pyritinol; quilostigmine; ribaminol; rivastigmine; rolziracetam; sabcomeline; sapropterin; SIB-1553A; sibopirdine; sipatrigine; SM-10888; SNK-882; SR-46559-A; stacofylline; T-588; T-82; TAK-147; talsaclidine; taltirelin; tamitinol; tenilsetam; vinconate; vinpocetine; xaliproden; xanomeline; YM-796; YM-900; Z-321; zifrosilone.

Mucolytics:
acetylcysteine; adamexine; ambroxol; bencisteine; bromhexine; brovanexine; carbocysteine; cartasteine; cistinexine; dacisteine; danosteine; dembrexine; domiodol; erdosteine; erythromycin salnacedin; erythromycin stinopate; guaimesal; IDB-1031; isalsteine; letosteine; mecysteine; mesna; midesteine; moguisteine; neltenexine; nesosteine; omonasteine; oxabrexine; prenisteine; salmisteine; stepronin; tasuldine; taurosteine; telmesteine; tiopronin.

Mydriatics:
berefrine.

Neuroprotective Agents:
dizocilpine maleate.

NMDA Antagonists:
ACPC; aptiganel; BMY-14802; CGP-37849; CP-101606; dizocilpine; EAA-090; eliprodil; felbamate; FPL-12495; gavestinel; harkoseride; HU-211; ipenoxazone; L-695902; lanicemine; licostinel; ligustizine; midafotel; milnacipran; nebostinel; remacemide; selfotel; seratrodast; spermidine; spermine; UK-240255; ZD-9379.

Nonhormonal Steroid Derivatives:
pregnenolone succinate.

Oxytocics:
carboprost; carboprost methyl; carboprost tromethamine; dinoprost; dinoprost tromethamine; dinoprostone; ergonovine maleate; meteneprost; methylergonovine maleate; oxytocin; sparteine sulfate.

Plasminogen Activators:
alteplase; urokinase.

PAF Antagonists:
lexipafant.

Aggregation Inhibitors:
acadesine; beraprost; beraprost sodium; ciprostene calcium; itazigrel; lifarizine; oxagrelate.

Progestins:
algestone acetophenide; amadinone acetate; anagestone acetate; chlormadinone acetate; cingestol; clogestone acetate; clomegestone acetate; desogestrel; dimethisterone; dydrogesterone; ethynerone; ethynodiol diacetate; etonogestrel; flurogestone acetate; gestaclone; gestodene; gestonorone caproate; gestrinone; haloprogesterone; hydroxyprogesterone caproate; levonorgestrel; lynestrenol; medrogestone; medroxyprogesterone acetate; methynodiol diacetate; norethindrone; norethindrone acetate; norethynodrel; norgestimate; norgestomet; norgestrel; oxogestone phenpropionate; progesterone; quingestanol acetate; quingestrone; tigestol.

Prostate Growth Inhibitors:
pentomone.

Prothyrotropin:
protirelin.

Psychotropic Agents:
minaprine.

Calcium Regulators:
alfacalcidol; calcifediol; calcipotriol; calcitonin; calcitriol; dihydrotachysterol; doxercalciferol; falecalcitriol; lexacalcitol; maxacalcitol; secalciferol; seocalcitol; tacalcitol;

Relaxants:
adiphenine; alcuronium chloride; aminophylline; azumolene sodium; baclofen; benzoctamine; carisoprodol; chlorphenesin carbamate; chlorzoxazone; cinflumide; cinnamedrine; clodanolene; cyclobenzaprine; dantrolene; dantrolene sodium; fenalamide; fenyripol; fetoxylate; flavoxate; fletazepam; flumetramide; flurazepam; hexafluorenium bromide; isomylamine; lorbamate; mebeverine; mesuprine; metaxalone; methocarbamol; methixene; nafomine malate; nelezaprine maleate; papaverine; pipoxolan; quinctolate; ritodrine; ritodrine; rolodine; theophylline sodium glycinate; thiphenamil; xilobam.

Scabicides:
amitraz; crotamiton.

Sclerosing Agents:
clobenoside; ethanolamine oleate; morrhuate sodium; olamine; tribenoside.

Sedatives:
propiomazine.

Hypnotics/Sedatives:
allobarbital; alonimid; alprazolam; amobarbital sodium; bentazepam; brotizolam; butabarbital; butabarbital sodium; butalbital; capuride; carbocloral; chloral betaine; chloral hydrate; chlordiazepoxide; cloperidone; clorethate; cyprazepam; dexclamol; diazepam; dichloralphenazone; estazolam; ethchlorvynol; etomidate; fenobam; flunitrazepam; fosazepam; glutethimide; halazepam; lormetazepam; mecloqualone; meprobamate; methaqualone; midaflur; paraldehyde; pentobarbital; pentobarbital sodium; perlapine; prazepam; quazepam; reclazepam; roletamide; secobarbital; secobarbital sodium; suproclone; thalidomide; tracazolate; trepipam maleate; triazolam; tricetamide; triclofos sodium; trimetozine; uldazepam; zaleplon; zolazepam; zolpidem tartrate.

Selective Adenosine A1 Antagonists:
apaxifylline

Serotonin Antagonists:
altanserin tartrate; amesergide; ketanserin; ritanserin, tropanserin Serotonin Inhibitors:
cinanserin; fenclonine; fonazine mesilate; xylamidine tosylate.

Stimulants:
amfonelic acid; amphetamine sulfate; ampyzine sulfate; arbutamine; azabon; caffeine; ceruletide; ceruletide diethylamine; cisapride; dazopride fumarate; dextroamphetamine; dextroamphetamine sulfate; difluanine; dimefline; doxapram; etryptamine acetate; ethamivan; fenethylline; flubanilate; flurothyl; histamine phosphate; indriline; mefexamide; methamphetamine hydrochloride; methylphenidate; pemoline; pyrovalerone; xamoterol; xamoterol fumarate.

Suppressants:
amflutizole; coxchicine; tazofelone.

Active Ingredients for Treating Symptomatic Multiple Sclerosis:
fampridine.

Synergistic Agents:
proadifen.

Thyroid Hormones:
levothyroxine sodium; liothyronine sodium; liotrix.

Thyroid Inhibitors:
methimazole; propyithiouracil.

Thyromimetics:
thyromedan.

Tranquilizers:
bromazepam; buspirone; chlordiazepoxide; clazolam; clobazam; clorazepate dipotassium; clorazepate monopotassium; demoxepam; dexmedetomidine; enciprazine; gepirone; hydroxyphenamate; hydroxyzine; hydroxyzine pamoate; ketazolam; lorazepam; lorzafone; loxapine; loxapine succinate; medazepam; nabilone; nisobamate; oxazepam; pentabamate; pirenperone; ripazepam; rolipram; sulazepam; taciamine; temazepam; triflubazam; tybamate; valnoctamide.

Agent for Treating Cerebral Ischemia:
dextrorphan.

Agent for Treating Paget's Disease:
tiludronate disodium.

Uricosuric Agents:
benzbromarone; irtemazole; probenecid; sulfinpyrazone.

Vasoconstrictors:
adrenalone; amidefrine mesilate; angiotensin amide; cafaminol; cilutazolin; clonazoline; corbadrine; domazoline; epinephrine; epinephryl borate; fenoxazoline; indanazoline; mephentermine; methysergide; metizoline; metrafazoline; naphazoline; nemazoline; oxedrine; oxymetazoline; phenamazoline; phenylephrine; phenylpropanolamine polistirex; tefazoline; tetryzoline; tinazoline; tramazoline; xylometazoline.

Vasodilators:
alprostadil; azaclorzine; bamethan sulfate; bepridil; buterizine; cetiedil citrate; chromonar; clonitrate; diltiazem; dipyridamole; droprenilamine; erythrityl tetranitrate; felodipine; flunarizine; fostedil; hexobendine; inositol niacinate; iproxamine; isosorbide dinitrate; isosorbide mononitrate; isoxsuprine; lidoflazine; mefenidil; mefenidil fumarate; mibefradil dihydrochloride; mioflazine; mixidine; nafronyl oxalate; nicardipine; nicergoline; nicorandil; nicotinyl alcohol; nifedipine; nimodipine; nisoldipine; oxfenicine; oxprenolol; pentaerythritol tetranitrate; pentoxifylline; pentrinitrol; perhexiline maleate; pindolol; pirsidomine; prenylamine; propatyl nitrate; suloctidil; terodiline; tiropidil; tolazoline; xanthinol niacinate.

Active Ingredients for Wound Healing:
ersofermin.

Xanthine Oxidase Inhibitors:
allopurinol; oxypurinol

In a preferred embodiment of the invention, the active ingredient is a PDE (phosphodiesterase) inhibitor, particularly preferably PDE 4 inhibitor, especially N-(3,5-dichloropyrid-4-yl)-3-cyclopropylmethoxy-4-difluoromethoxybenzamide (INN: roflumilast) its N-oxide or a pharmacologically suitable salt of roflumilast or of its N-oxide. The preparation of N-(3,5-dichloropyrid-4-yl)-3-cyclopropylmethoxy-4-difluoromethoxybenzamide, its pharmacologically suitable salts and its N-oxide, and the use of these compounds as phosphodiesterase (PDE) 4 inhibitors is described in the international application WO95/01338. In a particularly preferred embodiment of the invention, the active ingredient is a phosphodiesterase (PDE) 3/4 inhibitor, in particular (−)-cis-9-ethoxy-8-methoxy-6-(4-diisopropylaminocarbonylphenyl)-2-methyl-1,2,3,4,4a,10b-hexahydrobenzo[c][1,6]naphthyridine (INN: pumafentrine). The preparation of (−)-cis-9-ethoxy-8-methoxy-6-(4-diisopropylaminocarbonylphenyl)-2-methyl-1,2,3,4,4a,10b-hexahydrobenzo[c][1,6]naphthyridine and its pharmacologically suitable salts, and the use of this compound as phosphodiesterase (PDE) 3/4 inhibitor is described in the international application WO98/21208.

The matrix of the invention is outstandingly suitable as dosage form for active ingredients from the class of substances known as reversible $H^+$, $K^+$-ATPase inhibitors, which are also referred to as reversible proton pump inhibitors or APAs (acid pump antagonists). Reversible proton pump inhibitors or APAs are disclosed, for example, in the patent document DE-A3917232, EP-A-0399267, EP-A-0387821, JP-A-3031280, JP-A-2270873, EP-A-0308917, EP-A-0268989, EP-A-0228006, EP-A-0204285, EP-A-0165545, EP-A-0125756, EP-A-0120589, EP-A-0509974, DE-A 3622036, EP-A-0537532, EP-A-0535529, JP-A-3284686, JP-A-3284622, U.S. Pat. No. 4,833,149, EP-A-0261912, WO-A-9114677, WO-A-9315055, WO-A-9315071, WO-A-9315056, WO-A-9312090, WO-A-9212969, WO-A-9118887, EP-A-0393926, EP-A-0307078, U.S. Pat. No. 5,041,442, EP-A-0266890, WO-A-9414795, EP-A-0264883, EP-A-0033094, EP-A-0259174, EP-A-0330485, WO-A-8900570, EP-A-0368158, WO-A-9117164, WO-A-9206979, WO-A-9312090, WO-A-9308190, U.S. Pat. No. 5,665,730, DE-A 3011490, U.S. Pat. No. 4,464,372, EP-A-0068378, WO-A-9424130, U.S. Pat. No. 5,719,161, U.S. Pat. No. 6,124,313, WO-A-9527714, WO-A-9617830, WO-A-9837080, WO-A-9955705, WO-A-9955706, WO-A-0010999, WO-A-0011000, especially in the documents WO-A-9842707, WO-A-9854188, WO-A-0017200, WO-A-0026217 and WO-A-0063211, and in other patent documents which relate to compounds which inhibit gastric acid secretion and have a quinoline, imidazo[1,2-a]pyridine, 7,8,9,10-tetrahydroimidazo[1,2-h][1,7]naphthyridine or 7H-8,9-dihydropyrano[2,3-c]imidazo[1,2-a]pyridine basic structure.

Examples of reversible proton pump inhibitors or APAs which should be mentioned as preferred are, inter alia:

AU-461 [2-[1-(2-methyl-4-methoxyphenyl)-6-(2,2,2-trifluoroethoxy)-2,3-dihydro-1H-pyrrolo[3,2-c]quinolin-4-ylamino]-1-ethanol], DBM-819 [3-[1-(4-methoxy-2-methylphenyl)-6-methyl-2,3-dihydro-1H-pyrrolo-[3,2-c]quinolin-4-ylamino]1-propanol], KR-60436 [2-[1-(4-methoxy-2-methylphenyl)-6-(trifluoromethoxy)-2,3-dihydro-1H-pyrrolo[3,2-c]quinolin-4-ylamino]ethanol], R-105266; YJA-20379-8 [(+)-1-[8-ethoxy-4-[(1(R)-phenylethyl)amino]-1,7-naphthyridin-3-yl]-1-butanone], 8-(2-methoxycarbonylamino-6-methylbenzylamino)-2,3-dimethylimidazo[1,2-a]pyridine, 3-hydroxymethyl-8-(2-methoxycarbonylamino-6-methylbenzylamino)-2-methylimidazo[1,2-a]-pyridine, 3-hydroxymethyl-8-(2-methoxycarbonylamino-6-methylbenzyloxy)-2-methylimidazo[1,2-a]-pyridine, 8-(2-methoxycarbonylamino-6-methylbenzyloxy)-2,3-dimethylimidazo[1,2-a]pyridine, 8-(2-tert-butoxycarbonylamino-6-methylbenzylamino)-2,3-dimethylimidazo[1,2-a]pyridine, 8-(2-tert-butoxycarbonylamino-6-methylbenzyloxy)-2,3-dimethylimidazo[1,2-a]pyridine, 8-(2-ethoxycarbonylamino-6-methylbenzylamino)-2,3-dimethylimidazo[1,2-a]pyridine, 8-(2-isobutoxycarbonylamino-6-methylbenzylamino)-2,3-dimethylimidazo[1,2-a]pyridine, 8-(2-isopropoxycarbonylamino-6-methylbenzylamino)-2,3-dimethylimidazo[1,2-a]pyridine, 8-(2-tert-butoxycarbonylamino-6-methylbenzylamino)-3-hydroxymethyl-2-methylimidazo[1,2-a]-pyridine, 8-(2-tert-butoxycarbonylamino-6-methylbenzyloxy)-3-hydroxymethyl-2-methylimidazo[1,2-a]-pyridine, 8-{2-[(2-methoxyethoxy)carbonylamino]-6-methylbenzyloxy}-2-methylimidazo[1,2-a]pyridine-3-methanol, 8-{2-[(2-methoxyethoxy)carbonylamino]-6-methylbenzylamino}-2-methylimidazo[1,2-a]-pyridine-3-methanol, 8-{2-[(2-methoxyethoxy)carbonylamino]-6-methylbenzylamino}-2,3-dimethylimidazo[1,2-a]-pyridine, 8-{2-[(2-methoxyethoxy)carbonylamino]-6-methylbenzyloxy}-2-methylimidazo[1,2-a]pyridine-3-methanol, 8-{2-[(2-methoxyethoxy)carbonylamino]-6-methylbenzyloxy}-2,3-dimethylimidazo[1,2-a]pyridine, 3-hydroxymethyl-2-methyl-8-benzyloxyimidazo[1,2-a]pyridine, 3-hydroxymethyl-2-trifluoromethyl-8-benzyloxyimidazo[1,2-a]pyridine, 1,2-dimethyl-3-cyanomethyl-8-benzyloxyimidazo[1,2-a]pyridine, 2-methyl-3-cyanomethyl-8-benzyloxyimidazo[1,2-a]pyridine, 3-butyryl-8-methoxy-4-(2-methylphenylamino)quinoline, 3-butyryl-8-hydroxyethoxy-4-(2-methylphenylamino)quinoline, 3-hydroxymethyl-2-methyl-9-phenyl-7H-8,9-dihydropyrano[2,3-c]imidazo[1,2-a]pyridine, 3-hydroxymethyl-2-methyl-9-(4-fluorophenyl)-7H-8,9-dihydropyrano[2,3-c]imidazo[1,2-a]pyridine, (+)-3-hydroxymethyl-2-methyl-9-phenyl-7H-8,9-dihydropyrano[2,3-c]imidazo[1,2-a]pyridine, (−)-3-hydroxymethyl-2-methyl-9-phenyl-7H-8,9-dihydropyrano[2,3-c]imidazo[1,2-a]pyridine, 8-(2-ethyl-6-methylbenzylamino)-3-(hydroxymethyl)-2-methylimidazo[1,2-a]pyridine-6-carboxamide, N-(2-hydroxyethyl)-8-(2,6-dimethylbenzylamino)-2,3-dimethylimidazo[1,2-a]pyridine-6-carboxamide, 8-(2-ethyl-6-methylbenzylamino)-2,3-dimethylimidazo[1,2-a]pyridine-6-carboxamide, 8-(2-ethyl-6-methylbenzylamino)-N,2,3-trimethylimidazo[1,2-a]pyridine-6-carboxamide, 8-(2,6-dimethylbenzylamino)-2,3-dimethylimidazo[1,2-a]pyridine-6-carboxamide, 8-(2-ethyl-4-fluoro-6-methylbenzylamino)-2,3-dimethylimidazo[1,2-a]pyridine-6-carboxamide, 8-(4-fluoro-2,6-dimethylbenzylamino)-2,3-dimethylimidazo[1,2-a]pyridine-6-carboxamide, 8-(2,6-diethylbenzylamino)-2,3-dimethylimidazo[1,2-a]pyridine-6-carboxamide, 8-(2-ethyl-6-methylbenzylamino)-N-(2-hydroxyethyl)-2,3-dimethylimidazo[1,2-a]pyridine-6-carboxamide, 8-(2-ethyl-6-methylbenzylamino)-N-(2-methoxyethyl)-2,3-dimethylimidazo[1,2-a]pyridine-6-carboxamide, 8-(2-ethyl-6-methylbenzylamino)-3-(hydroxymethyl)-2-methylimidazo[1,2-a]pyridine-6-carboxamide, N-(2-hydroxyethyl)-8-(2,6-dimethylbenzylamino)-2,3-dimethylimidazo[1,2-a]pyridine-6-carboxamide, 8-(2-ethyl-6-methylbenzylamino)-2,3-dimethylimidazo[1,2-a]pyridine-6-carboxamide, 8-(2-ethyl-6-methylbenzylamino)-N,2,3-trimethylimidazo[1,2-a]pyridine-6-carboxamide, 8-(2,6-dimethylbenzylamino)-2,3-dimethylimidazo[1,2-a]pyridine-6-carboxamide, 8-(2-ethyl-4-fluoro-6-methylbenzylamino)-2,3-dimethylimidazo[1,2-a]pyridine-6-carboxamide, 8-(4-fluoro-2,6-dimethylbenzylamino)-2,3-dimethylimidazo[1,2-a]pyridine-6-carboxamide, 8-(2,6-diethylbenzylamino)-2,3-dimethylimidazo[1,2-a]pyridine-6-carboxamide, 8-(2-ethyl-6-methylbenzylamino)-N-(2-hydroxyethyl)-2,3-dimethylimidazo[1,2-a]pyridine-6-carboxamide and 8-(2-ethyl-6-methylbenzylamino)-N-(2-methoxyethyl)-2,3-dimethylimidazo[1,2-a]pyridine-6-carboxamide, and, in particular, 7,8-dihydroxy-2,3-dimethyl-9-phenyl-7,8,9,10-tetrahydroimidazo[1,2-h][1,7]naphthyridine, 7-hydroxy-2,3-dimethyl-9-phenyl-7,8,9,10-tetrahydroimidazo[1,2-h][1,7]naphthyridine, 9-(2-chlorophenyl)-7-hydroxy-2,3-dimethyl-7,8,9,10-tetrahydroimidazo[1,2-h][1,7]naphthyridine, 9-(2,6-dichlorophenyl)-7-hydroxy-2,3-dimethyl-7,8,9,10-tetrahydroimidazo[1,2-h][1,7]naphthyridine, 9-(2-trifluoromethylphenyl)-7-hydroxy-2,3-dimethyl-7,8,9,10-tetrahydroimidazo[1,2-h][1,7]naphthyridine, 8-hydroxy-2,3-dimethyl-9-phenyl-7,8,9,10-tetrahydroimidazo[1,2-h][1,7]naphthyridin-7-one, (8R,9R)-3-formyl-8-hydroxy-2-methyl-7-oxo-9-phenyl-7,8,9,10-tetrahydroimidazo[1,2-h][1,7]naphthyridine, (7R,8R,9R)-3-hydroxymethyl-7,8-dihydroxy-2-methyl-9-phenyl-7,8,9,10-tetrahydroimidazo[1,2-h][1,7]-naphthyridine, (7S,8R,9R)-7,8-isopropylidenedioxy-2,3-dimethyl-9-phenyl-7,8,9,10-tetrahydroimidazo[1,2-h][1,7]naphthyridine, 8,9-trans-8-hydroxy-3-hydroxymethyl-2-methyl-9-phenyl-7H-8,9-dihydropyrano[2,3-c]imidazo[1,2-a]-pyridine, 8,9-cis-8-hydroxy-3-hydroxymethyl-2-methyl-9-phenyl-7H-8,9-dihydropyrano[2,3-c]imidazo[1,2-a]-pyridine, 8,9-trans-3-hydroxymethyl-8-methoxy-2-methyl-9-phenyl-7H-8,9-dihydropyrano-[2,3-c]imidazo[1,2-a]-pyridine, 8,9-cis-3-hydroxymethyl-8-methoxy-2-methyl-9-phenyl-7H-8,9-dihydropyrano[2,3-c]imidazo[1,2-a]-pyridine, 8,9-trans-8-ethoxy-3-hydroxymethyl-2-methyl-9-phenyl-7H-8,9-dihydropyrano[2,3-c]imidazo[1,2-a]-pyridine, 8-hydroxy-7-oxo-9-phenyl-2,3-dimethyl-7H-8,9-dihydropyrano[2,3-c]imidazo[1,2-a]pyridine, 7,8-dihydroxy-9-phenyl-2,3-dimethyl-7H-8,9-dihydropyrano[2,3-c]imidazo[1,2-a]pyridine, 7-hydroxy-9-phenyl-2,3-dimethyl-7H-8,9-dihydropyrano[2,3-c]imidazo[1,2-a]pyridine, (7R,8R,9R)-2,3-dimethyl-8-hydroxy-7-methoxy-9-phenyl-7,8,9,10-tetrahydroimidazo[1,2-h]-[1,7]naphthyridine, (7S,8S,9S)-2,3-dimethyl-8-hydroxy-7-methoxy-9-phenyl-7,8,9,10-tetrahydroimidazo[1,2-h]-[1,7]naphthyridine, (7S,8R,9R)-2,3-dimethyl-8-hydroxy-7-methoxy-9-phenyl-7,8,9,10-tetrahydroimidazo[1,2-h][1,7]naphthyridine, (7R,8S,9S)-2,3-dimethyl-8-hydroxy-7-methoxy-9-phenyl-7,8,9,10-tetrahydroimidazo[1,2-h]-[1,7]naphthyridine, (7R,8R,9R)-2,3-dimethyl-7-ethoxy-8-hydroxy-9-phenyl-7,8,9,10-tetrahydroimidazo[1,2-h]-[1,7]naphthyridine, (7S,8R,9R)-2,3-dimethyl-7-ethoxy-8-hydroxy-9-phenyl-7,8,9,10-tetrahydroimidazo[1,2-h]-[1,7]naphthyridine, (7S,8S,9S)-2,3-dimethyl-8-hydroxy-7-(2-methoxyethoxy)-9-phenyl-7,8,9,10-tetrahydroimidazo[1,2-h]-[1,7]naphthyridine, (7S,8R,9R)-2,3-dimethyl-8-hydroxy-7-(2-methoxyethoxy)-9-phenyl-7,8,9,10-tetrahydroimidazo[1,2-h]-[1,7]naphthyridine, (7R,8S,9S)-2,3-dimethyl-8-hydroxy-7-(2-methoxyethoxy)-9-phenyl-7,8,9,10-tetrahydroimidazo[1,2-h]-[1,7]naphthyridine, (7S,8R,9R)-2,3-dimethyl-8-hydroxy-9-phenyl-7-(2-propoxy)-7,8,9,10-tetrahydroimidazo[1,2-h][1,7]-naphthyridine, (7R,8R,9R)-2,3-dimethyl-7,8-dimethoxy-9-phenyl-7,8,9,10-tetrahydroimidazo[1,2-h][1,7]naphthyridine, (7R,8R,9R)-2,3-dimethyl-8-hydroxy-7-(2-methylthioethyloxy)-9-phenyl-7,8,9,10-tetrahydroimidazo[1,2-h][1,7]naphthyridine, (7S,8R,9R)-2,3-dimethyl-8-hydroxy-7-(2-methylthioethyloxy)-9-phenyl-7,8,9,10-tetrahydroimidazo[1,2-h][1,7]naphthyridine, (7R,8R,9R)-2,3-dimethyl-8-hydroxy-7-(2-methylsulfinylethoxy)-9-phenyl-7,8,9,10-tetrahydroimidazo-[1,2-h][1,7]naphthyridine, (7S,8R,9R)-2,3-dimethyl-8-hydroxy-7-(2-methylsulfinylethoxy)-9-phenyl-7,8,9,10-tetrahydroimidazo-[1,2-h][1,7]naphthyridine, (7R,8R,9R)-2,3-dimethyl-8-hydroxy-7-(ethylthio)-9-phenyl-7,8,9,10-tetrahydroimidazo[1,2-h][1,7]-naphthyridine, (7S,8R,9R)-2,3-dimethyl-8-hydroxy-7-(ethylthio)-9-phenyl-7,8,9,10-tetrahydroimidazo[1,2-h][1,7]-naphthyridine, (7R,8R,9R)-2,3-dimethyl-8-hydroxy-7-(2,2,2-trifluoroethoxy)-9-phenyl-7,8,9,10-tetrahydroimidazo-[1,2-h][1,7]naphthyridine and (7S,8R,9R)-2,3-dimethyl-8-hydroxy-7-(2,2,2-trifluoroethoxy)-9-phenyl-7,8,9,10-tetrahydroimidazo-[1,2-h][1,7]naphthyridine, and very particularly (7R,8R,9R)-2,3-dimethyl-7,8-dihydroxy-9-phenyl-7,8,9,10-tetrahydroimidazo[1,2-h][1,7]naphthyridine and (7R,8R,9R)-2,3-dimethyl-8-hydroxy-7-(2-methoxyethoxy)-9-phenyl-7,8,9,10-tetrahydroimidazo[1,2-h]-[1,7]naphthyridine.

The matrix of the of the invention is also outstandingly suitable as dosage form for active ingredients from the class of substances known as acid-labile $H^+$, $K^+$-ATPase inhibitors, which are also referred to as irreversible proton pump inhibitors. Acid-labile proton pump inhibitors ($H^+/K^+$-ATPase inhibitors) which may be particularly mentioned for the purpose of the present invention are substituted pyridin-2-ylmethylsulfinyl-1H-benzimidazoles as disclosed, for example, in EP-A-0 005 129, EP-A-0 166 287, EP-A 0 174 726, EP-A-0 184 322, EP-A-0 261 478 and EP-A-0 268 956. Those which may be mentioned as preferred in this conenction are 5-methoxy-2-[(4-methoxy-3,5-dimethyl-2-pyridinyl)-methylsulfinyl]-1H-benzimidazole (INN: omeprazole), 5-difluoromethoxy-2-[(3,4-dimethoxy-2-pyridinyl)-methylsulfinyl]-1H-benzimidazole (INN: pantoprazole), 2-[3-methyl-4-(2,2,2-trifluoroethoxy)-2-pyridinyl)methylsulfinyl]-1H-benzimidazole (INN: lansoprazole) and 2-{[4-(3-methoxypropoxy)-3-methylpyridin-2-yl]methylsulfinyl}-1H-benzimidazole (INN: rabeprazole). Further acid-labile proton pump inhibitors, for example substituted phenylmethylsulfinyl-1H-benzimidazoles, cycloheptapyridin-9-ylsulfinyl-1H-benzimidazoles or pyridin-2-ylmethylsulfinylthienoimidazoles, are disclosed in DE-A-35 31 487, EP-A-0 434 999 and EP-A-0 234 485 respectively. Examples which may be mentioned are 2-[2-(N-isobutyl-N-methylamino) benzylsulfinyl]benzimidazole (INN: leminoprazole) and 2-(4-methoxy-6,7,8,9-tetrahydro-5H-cyclohepta[b]pyridin-9-ylsulfinyl)-1H-benzimidazole (INN: nepaprazole). The acid-labile proton pump inhibitors are chiral compounds. The term acid-labile proton pump inhibitor also encompasses the pure enantiomers of the acid-labile proton pump inhibitors and their mixtures in any mixing ratio. Pure enantiomers which may be mentioned by way of example are 5-methoxy-2-[(S)-[(4-methoxy-3,5-dimethyl-2-pyridinyl)methyl]sulfinyl]-1H-benzimidazole (INN: esomeprazole) and (−)-pantoprazole. The acid-labile proton pump inhibitors are moreover present as such or, preferably, in the form of their salts with bases. Examples of salts with bases which may be mentioned are sodium, potassium, magnesium or calcium salts. If the acid-labile proton pump inhibitors are isolated in crystalline form, they may contain variable amounts of solvent. The term acid-labile proton pump inhibitor therefore also represents according to the invention all solvates, in particular all hydrates, of the acid-labile proton pump inhibitors and their salts. Such a hydrate of the salt of an acid-labile proton pump inhibitor with a base is disclosed, for example, in WO91/19710. Acid-labile proton pump inhibitors which may be mentioned as particularly preferred are pantoprazole sodium sesquihydrate (=pantoprazole sodium×1.5 $H_2O$), (−)-pantoprazole sodium sesquihydrate, pantoprazole magnesium dihydrate, omeprazole magnesium, omeprazole and esomeprazole.

In another preferred embodiment of the invention, the active ingredient is a glucocorticosteroid, in particular ciclesonide.

The active ingredients may, depending on the nature of the active ingredient, also be present in the preparations of the invention in the form of a salt of the active ingredient. Particular mention may be made of the pharmacologically suitable salts of the inorganic and organic acids normally used in pharmaceutical technology. Suitable as such are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)-benzoic acid, butyric acid, sulfosalicylic acid, maleic acid, lauric acid, malic acid, fumaric acid, succinic acid, oxalic acid, tartaric acid, embonic acid, stearic acid, toluene sulfonic acid, methanesulfonic acid or 3-hydroxy-2-naphthoic acid, the acids being employed for preparing the salts in the equimolar ratio of amounts, or a ratio differing therefrom,—depending on whether the acid is monobasic or polybasic and depending on which salt is required.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, the bases being employed for preparing the salts also in the equimolar ratio of amounts or in a ratio differing therefrom.

The skilled worker is aware that active ingredients and their salts may, if they are isolated, for example, in crystalline form, contain various amounts of solvents. The active ingredients will therefore also be present in the preparations of the invention in the form of solvates and, in particular, hydrates, and in the form of solvates and, in particular, also hydrates of the salts of the active ingredients.

The active ingredients may also be chiral compounds. It is therefore also possible for the pure enantiomers of the active ingredients and mixtures thereof in any mixing ratio to be present in the preparations of the invention.

The fatty alcohol is preferably a linear, saturated or unsaturated primary alcohol with 10-30 carbon atoms. It is preferably a primary alcohol with 10 to 18 carbon atoms in linear chains. Examples of fatty alcohols which may be mentioned are cetyl alcohol, myristyl alcohol, lauryl alcohol or stearyl alcohol, with preference for cetyl alcohol. It is also possible if desired for mixtures of fatty alcohols to be present.

The triglyceride is glycerol with its three hydroxyl groups esterified by carboxylic acids. The carboxylic acids are preferably monobasic carboxylic acids with 8 to 22 carbon atoms, preferably naturally occurring carboxylic acids. It is possible in this case for the carboxylic acids to be different or, preferably, identical. Examples which may be mentioned are tristearate, tripalmitate and, particularly preferably, trimyristate (these triglycerides are commercially available under the name Dynasan 118, 116 and 114 respectively). It is also possible if desired for mixtures of triglycerides to be present.

The fatty acid ester is the ester of an alcohol with a fatty acid. The alcohol in this case is preferably a linear, saturated or unsaturated primary alcohol with 10-30, preferably with 12 to 18, carbon atoms. The fatty acid is preferably a monobasic carboxylic acid with 8 to 22, in particular 12 to 18, carbon atoms, preferably a naturally occurring carboxylic acid. Fatty acid esters preferred according to the invention have a melting point above 30° C. Examples of fatty acid esters which may be mentioned are cetyl palmitate, which is commercially available for example under the name Cutina® CP. It is also possible if desired for mixtures of fatty acid esters to be present.

The solid paraffin is preferably paraffinum solidum (ceresin). It is also possible alternatively to use ozokerite, for example. It is also possible if desired to use mixtures.

The partial glyceride is according to the invention glycerol in which one or two hydroxyl groups are esterified by carboxylic acids. The carboxylic acids are preferably monobasic carboxylic acids with 8 to 22 carbon atoms, preferably naturally occurring carboxylic acids, in particular stearic acid, palmitic acid and myristic acid. It is possible in this case for the carboxylic acids to be different or, preferably, the same. Examples which may be mentioned are glycerol monostearate, glycerol distearate and glycerol monopalmitate, glycerol dipalmitate. It is also possible if desired for mixtures of partial glycerides to be present.

If desired, the mixtures in the individual active ingredient units may include one or more other pharmaceutically suitable excipients. Other suitable excipients which may be mentioned by way of example are polymers, sterols and—in the case of acid-labile active ingredients—basic compounds.

Examples of polymers which may be mentioned are povidone (e.g. Kollidon® 17, 30 and 90 from BASF), vinylpyrrolidone/vinyl acetate copolymer and polyvinyl acetate. Others which may be mentioned are cellulose ethers [such as, for example, methylcellulose, ethylcellulose (Ethocel®) and hydroxypropylmethylcellulose], cellulose esters [such as cellulose acetate phthalate (CAP), cellulose acetate trimellitate (CAT), hydroxypropylmethylcellulose phthalate (HP50 and HP55) or hydroxypropylmethylcellulose acetate succinate (HPMCAS)], methacrylic acid/methyl methacrylate copolymer or methacrylic acid/ethyl methacrylate copolymer (Eudragit® L). The polymer is preferably povidone or ethylcellulose. It is also possible if desired for mixtures of polymers to be present. It is possible by adding suitable polymers, for example, to influence the pharmaceutical properties of the individual active ingredient units (e.g. delivery of the active ingredient). Particularly preferred polymers according to the invention are povidone or ethylcellulose.

The sterol is preferably a phytosterol or a zoosterol. Examples of phytosterols which may be mentioned are ergosterol, stigmasterol, sitosterol, brassicasterol and campesterol. Examples of zoosterols which may be mentioned are cholesterol and lanosterol. It is also possible if desired for mixtures of sterols to be present.

Examples of suitable basic compounds are inorganic basic salts such as ammonium carbonate and sodium carbonate, salts of fatty acids such as sodium stearate, amines such as meglumine, di-, triethylamine and TRIS(2-amino-2-hydroxymethyl-1,3-propanediol) or fatty amines such as stearylamine. Stearylamine and sodium stearate may be mentioned as preferred. The addition of basic compounds to the mixtures in the individual units results, in the case of acid-labile active ingredients, in particularly stable preparations and prevents possible discolorations.

The proportion (in percent by weight) of active ingredient in the individual active ingredient unit depends on the type of active ingredient and is advantageously 0.01-90%. The proportion of active ingredient is preferably 0.1-70%, particularly preferably 5-40%, in particular 10-20%. The proportion of fatty alcohol in the individual active ingredient unit is advantageously 10-70%, preferably 20-70%, particularly preferably 20-60% and in particular 30-60%. The proportion of triglyceride in the individual active ingredient unit is advantageously 10-70%, preferably 20-70%, particularly preferably 20-60% and in particular 30-60%. The proportion of partial glyceride in the individual active ingredient unit is advantageously 10-70%, preferably 20-70%, particularly preferably 20-60% and in particular 30-60%. The proportion of fatty acid ester in the individual active ingredient unit is advantageously 10-70%, preferably 20-70%, particularly preferably 20-60% and in particular 30-60%. The proportion of solid paraffin is advantageously 10-70%, preferably 20-60% and in particular 30-60%. If present, the proportion of polymer in the individual active ingredient unit is expediently 1-25%, preferably 1-10%, particularly preferably 5-10%. If present, the proportion of sterol is expediently 1-10%, preferably 1-5%. If present, the proportion of basic compound is 0.05-5%, preferably 0.1-1%.

Preferred individual active ingredient units of the invention consist of 2-70% active ingredient, 10-60% fatty alcohol, 10-60% solid paraffin and 1-15% polymer. Further preferred individual active ingredient units of the invention consist of 2-70% active ingredient, 10-60% triglyceride, 10-60% solid paraffin, 1-15% polymer. Other preferred individual active ingredient units of the invention consist of 2-70% active ingredient, 10-60% fatty acid ester, 10-60% solid paraffin and 1-15% polymer.

In one embodiment, the invention relates to a preparation in which an active ingredient is essentially uniformly distributed in an excipient matrix composed of a mixture of at least one solid paraffin, a fatty alcohol, a fatty acid ester and a partial glyceride or triglyceride. Such preparations preferably consist of 0.05 to 25% active ingredient, 10 to 70% solid paraffin, 5 to 80% fatty alcohol, 2 to 20% fatty acid ester and 5 to 80% triglyceride or partial glyceride. Such preparations consist, in particular, of 0.1 to 20% active ingredient, 15 to 65% solid paraffin, 5 to 70% fatty alcohol, 2 to 15% fatty acid ester and 5 to 70% triglyceride or partial glyceride. Such preparations particularly preferably consist of 0.5 to 15% active ingredient, 15 to 60% solid paraffin, 5 to 50% fatty alcohol, 5 to 10% fatty acid ester and 10 to 50% triglyceride or partial glyceride.

In another embodiment, the invention relates to a preparation in which an active ingredient is essentially uniformly dispersed in an excipient matrix composed of at least one fatty alcohol together with at least one excipient selected from the group of solid paraffin or polymer. The polymer is preferably ethylcellulose or povidones. Such preparations preferably consist of 0.05 to 25% active ingredient, 20 to 90% fatty alcohol, 10 to 80% solid paraffin and/or 0.05 to 2% ethylcellulose. Such preparations consist in particular of 0.1 to 20% active ingredient, 25 to 80% fatty alcohol, 10 to 70% solid paraffin and/or 0.1 to 1.5% ethylcellulose. Such preparations particularly preferably consist of 0.5 to 15% active ingredient, 25 to 70% fatty alcohol, 10 to 60% solid paraffin and/or 0.2 to 1% ethylcellulose.

In the case of acid-labile active ingredients, in particular the acid-labile proton pump inhibitors, preferred individual active ingredient units of the invention consist of 2-70% active ingredient, 10-60% fatty alcohol, 10-60% solid paraffin, 1-15% polymer and 0.1-2% of a basic compound. Further preferred individual active ingredient units of the invention consist of 2-70% active ingredient, 10-60% triglyceride, 10-60% solid paraffin, 1-15% polymer and 0.1-2% of a basic compound. Other preferred individual active ingredient units of the invention consist of 2-70% active ingredient, 10-60% fatty acid ester, 10-60% solid paraffin, 1-15% polymer and 0.1-2% of a basic compound. Particularly preferred individual active ingredient units of the invention consist of 5-40% active ingredient, 20-60% fatty alcohol, 10-60% solid paraffin, 1-15% polymer and 0.1-1% of a basic compound. Further particularly preferred individual active ingredient units of the invention consist of 5-40% active ingredient, 20-60% triglyceride, 10-60% solid paraffin, 1-15% polymer and 0.1-1% of a basic compound. Other particularly preferred individual active ingredient units of the invention consist of 5-40% active ingredient, 20-60% fatty acid ester, 10-60% solid paraffin, 1-15% polymer and 0.1-1% of a basic compound.

Examples of active ingredient units of the invention contain 5-40% pantoprazole sodium sesqulhydrate, 10-40% cetyl alcohol, 5-60% solid paraffin, 1-5% polymer and 0.1-0.2% of a basic compound. Further examples of active ingredient units of the invention contain 5-40% pantoprazole sodium sesquihydrate, 10-40% glyceryl tripalmitate, 5-60% solid paraffin, 1-5% polymer and 0.1-0.2% of a basic compound. Other examples of active ingredient units of the invention contain 5-40% pantoprazole sodium sesquihydrate, 10-40% glyceryl tripalmitate, 5-60% solid paraffin, 1-5% polymer and 0.1-0.2% of a basic compound. Still other examples of active ingredient units of the invention contain 10-20% pantoprazole sodium sesquihydrate, 20-40% triglyceride, 40-70% solid paraffin, 1-5% sterol and 0.05-0.1% of a basic compound.

The individual active ingredient units can be produced for example by spray drying or, preferably, by spray solidification, in particular also by spray prilling. Production is particularly preferably by prilling, in particular by vibration prilling.

For the spray solidification or prilling expediently the matrix excipients are liquefied to give a melt. The active ingredient is dissolved or dispersed in this solution, and the resulting solution or dispersion is sprayed or, preferably, prilled in a suitable apparatus. A dispersion of the active ingredient in a melt of the excipients is preferably used.

Spray solidification takes place in a manner known per se. A detailed description of this technique is to be found in P. B. Deasy, Microencapsulation and Related Drug Processes (1984).

The individual active ingredient units are particularly preferably produced by solidification from liquid phase by generating drops by means of vibrating nozzles and by solidifying the drops which are formed, after they have stabilized, by drying or cooling in a suitable medium (preferably gaseous or liquid). The suitable medium may be, for example, cooled gas such as air or nitrogen. Processes of this type and corresponding apparatuses are disclosed in DE 27 25 924, EP 0 467 221, WO99/33555 and WO00/24382.

It is particularly preferred according to the invention in the prilling process for the liquid phase flowing to the nozzle to be kept at a constant temperature. The solidification preferably takes place by instantaneous cooling in a suitable cooling medium. In prilling, moreover, it is preferred for the liquid phase flowing to the nozzle, the vibrating nozzle and the drops formed by prilling to be kept at a constant temperature until their spherical shape has stabilized, and for the solidification of the drops after their stabilization to be carried out instantaneously by cooling with a gaseous or liquid cooling medium. Systems suitable for prilling by means of vibrating nozzles are marketed, for example, by Brace GmbH, Aizenau, Germany. It is possible by means of prilling using vibrating nozzles to obtain the individual active ingredient units in the form of microspheres with a narrow monomodal particle size spectrum in the particle size range from 50 µm to 2 mm. The narrow monomodal particle size spectrum and the uniform spherical shape of the microspheres obtained in this way are expected to result in a uniformly smooth surface, a uniform, defined delivery of active ingredient and, in relation to passage through the stomach in the case of oral dosage forms (owing to the small particles), a behavior like that of a solution. The microspheres of the invention are distinguished in particular by high stability, a release of active ingredient which can be controlled via the particle size and composition of the matrix, good flow characteristics, good compressibility and a uniform delivery of active ingredient. It is particularly worthy of mention that the microspheres can be further processed to a large number of pharmaceutical dosage forms without thereby losing a given functionality (such as taste masking, resistance to gastric juice, slowing of release).

The microspheres are preferably monomodal microspheres with a particle size range of 50-800 µm, preferably 50-500 µm, particularly preferably 50-400 µm, in particular 50-200 µm.

The particle size of the active ingredient employed in the spray drying or spray solidification, prilling or vibration prilling is advantageously less than or equal to 100 µm, in particular less than 40 µm. The particle size is preferably in the range 1-20 µm, particularly preferably in the range 3-15 µm. Such a particle size can be achieved, for example, by grinding the active ingredient in a suitable mill.

The individual active ingredient units (preparations) of the invention can then be used as basis for producing the dosage forms of the invention. Examples which may be mentioned are dosage forms of the invention, to which the preparations can be processed, as suspensions, gels, tablets, coated tablets, multicomponent tablets, effervescent tablets, rapidly disintegrating tablets, powders in sachets, coated tablets, capsules, solutions or else suppositories. Preferred dosage forms in this connection are oral dosage forms, in particular tablets. Particular preference is given to rapidly disintegrating tablets and effervescent tablets. The excipients suitable for the desired dosage forms are familiar to the skilled worker on the basis of his expert knowledge. In the case of oral dosage forms it is surprisingly possible to dispense with the enteric coating.

In the case of rapidly disintegrating tablets, suitable excipients are, in particular, those excipients which on oral intake of the tablet bring about rapid disintegration of the tablets. Excipients which on oral intake of the tablet bring about rapid disintegration of the tablet preferably comprise one or more substances selected from the group of fillers and disintegrants. One or more other excipients from the group of lubricants, flavors, flavoring substances and surface-active substances are preferably present in the rapidly disintegrating dosage form of the invention. Binders can also be present if desired. The rapidly disintegrating dosage form particularly preferably comprises a mixture of at least one filler, one disintegrant and one lubricant. Fillers suitable according to the invention are, in particular, basic fillers such as calcium carbonate (e.g. MagGran® CC or Destab® 95) and sodium carbonate, sugar alcohols such as mannitol (e.g. Pearlitol® or Parteck® M), sorbitol (e.g. Karion®), xylitol or maltitol, starches such as corn starch, potato starch and wheat starch, microcrystalline cellulose, saccharides such as glucose, lactose, levulose, sucrose and dextrose. In a preferred development of the invention, the rapidly disintegrating dosage form of the invention comprises as filler a mixture of a basic filler (in particular calcium carbonate) and a sugar alcohol (in particular sorbitol or mannitol). Disintegrants suitable according to the invention are, in particular, insoluble polyvinylpyrrolidone (insoluble PVP, crospovidone), sodium carboxymethylstarch, sodium carboxymethylcellulose, alginic acid and starches able to carry out the function of a disintegrant (e.g. Starch 1500). Suitable lubricants which may be mentioned are sodium stearyl fumarate, magnesium stearate, calcium stearate, stearic acid, talc and highly disperse silica (Aerosil). Suitable surface-active substances which may be mentioned are sodium lauryl sulfate or Tween® 20, 60 or 80. Binders suitable according to the invention are polyvinylpyrrolidone (PVP, Polyvidon® K25, 90) or mixtures of PVP with polyvinyl acetate (e.g. Kollidon® 64), gelatin, corn starch mucilage, preswollen starches (Starch 1500), hydroxypropylmethylcellulose (HPMC) or hydroxypropylcellulose (L-HPC).

The proportion (in percent by weight based on the finished tablet) of filler in the rapidly disintegrating tablet is advantageously from 1 to 99% by weight. The proportion of filler is preferably from 30 to 95% by weight, and the proportion is very particularly preferably from 60 to 85% by weight.

The proportion (in percent by weight based on the finished tablet) of disintegrant in the rapidly disintegrating tablet is usually from 1 to 30% by weight. The proportion of disintegrant is preferably from 2 to 15% by weight. The proportion of disintegrant is particularly preferably from 5 to 10% by weight.

The proportion (in percent by weight based on the finished tablet) of lubricant in the rapidly disintegrating tablet is usually from 0.1 to 5% by weight. The proportion of lubricant is preferably from 0.3 to 3% by weight. The proportion of lubricant is particularly preferably from 0.5 to 2% by weight.

The proportion (in percent by weight based on the finished tablet) of individual active ingredient units in the rapidly disintegrating tablet is usually from 1 to 90% by weight. The proportion of individual active ingredient units is preferably up to 70% by weight, in particular from 10 to 50% by weight. The proportion is very particularly preferably from 15 to 25% by weight.

The proportion (in percent by weight based on the finished tablet) of binder can be up to 10% by weight, and it can preferably be up to 5% by weight.

If desired, one or more flavoring substances (e.g. flavors or sweeteners) can additionally be present in the rapidly disintegrating tablet. This makes it possible, for example, to achieve an improvement of the taste of the rapidly disintegrating tablet. These substances are added in conventional amounts.

The rapidly disintegrating tablet is produced by processes known to the skilled worker. The rapidly disintegrating tablet is preferably produced by i) dry mixing of filler and/or disintegrant;

ii) production of granules of filler and binder and mixing of the granules with a disintegrant or iii) dry granulation (briqueting or compacting) of one or more excipient components.

The individual active ingredient units are subsequently admixed to the mixtures obtained in i), ii) or iii) and then, if desired, flavors/flavoring substances and finally also one or more lubricants are admixed. The mixture obtained in this way can be compressed in a tablet press under conventional conditions.

Rapid disintegration of the tablet means according to the invention disintegration of the tablet in about 60 seconds or less when the tablet is subjected to a disintegration test as described in the European Pharmacopoeia (3rd edition, 1997) 2.9.1 disintegration time of tablets and capsules.

In the case of solutions and suspensions, suitable excipients are, in particular, those excipients which are normally used to produce solutions or suspensions. Particularly suitable according to the invention are excipients with which it is possible to produce a thickened base, such as thickeners. Examples of thickeners of the invention are xanthan, substituted celluloses, polyvinylpyrrolidone (polyvidone types), sheet silicates, alginates or alginic acids. Also possible if desired is a mixture of two or more different thickeners. The proportion of thickener depends on the desired viscosity or consistency intended for the solution or suspension ready for use. A solution or suspension with a viscosity of less than 500 mPa·s (determined with a rotational viscometer) is particularly preferred. The proportion of xanthan, based on the solution or suspension ready for use, is usually from 0.1 to 1% by weight. The proportion of substituted celluloses depends on the viscosity levels of the celluloses and is usually from 0.1 to 10% by weight based on the solution or suspension ready for use. Examples of substituted celluloses of the invention which may be mentioned are carboxymethylcellulose, ethylcellulose or methylcellulose or hydroxypropylcellulose. The proportion of polyvinylpyrrolidone (polyvidone types) is normally from 0.1 to 10% by weight based on the solution or suspension ready for use. Sheet silicates such as the Veegum or bentonites can be employed alone or in combination with water-soluble thickeners. The total proportion of thickener is then advantageously from 0.1 to 7% by weight based on the solution or suspension ready for use. Alginates and alginic acid are usually added in a proportion of from 0.1 to 10% by weight based on the solution or suspension ready for use. Further pharmaceutical excipients preferably employed are insoluble, crosslinked polyvinylpyrrolidone (crospovidones) and microcrystalline cellulose. It is observed in this case that a loose sediment forms and prevents agglomeration of the individual active ingredient units. The ratio of crospovidones to the individual active ingredient units is advantageously from 1:1 to 0.5:1 (based on weight). Microcrystalline cellulose, which is normally employed in a proportion of from 0.5 to 5% by weight based on the solution or suspension ready for use, is likewise suitable for this purpose. The proportion of individual active ingredient units in the solution or suspension ready for use is usually according to the invention from 1 to 20% by weight based on the solution or suspension ready for use, preferably 1 to 15% by weight and very preferably 5 to 10%. Water is preferably used as solvent or dispersant for the solution or suspension.

Other suitable excipients which may be present in the solution or suspension of the invention are, for example, flavoring substances (such as flavors and sweeteners), buffer substances, preservatives or else emulsifiers. Flavors are usually added in a proportion of from 0.05 to 1% by weight. Other flavoring substances by way of example are acids such as citric acid, sweeteners such as saccharin, aspartame, cyclamate sodium or maltol, which are added according to the desired result. Examples of emulsifiers are lecithins, sodium lauryl sulfate, Tweens® or Spans, which are normally added in a proportion of from 0.01 to 1% by weight. Preservatives such as benzoic acid, salts of benzoic acid, methyl 4-hydroxybenzoate, propyl 4-hydroxybenzoate, sorbic acid or salts thereof are preferably also added. The proportion depends on the preservative used and is normally from 0.1 to 4% by weight based on the solution or suspension ready for use.

The solution or suspension of the invention is produced by techniques known to the skilled worker. If a powder for reconstitution is to be produced, preferably a mixture of the individual active ingredient units with the thickener and, where appropriate, further excipients is produced. This powdered mixture for reconstitution is then mixed with a suitable amount of water immediately before administration. Solution or suspension ready for use is normally produced by introducing the individual active ingredient units into a dispersion of the thickener and, where appropriate, of additives in water or, alternatively, by introducing the thickener into a dispersion of the individual active ingredient units in water.

In a preferred embodiment, the invention relates to rapidly disintegrating tablets or solutions or suspension which comprise preparations of the invention with PDE inhibitors as active ingredients. Preferred PDE inhibitors in this case are roflumilast and pumafentrine.

The dosage forms of the invention can be employed for the treatment and prevention of all diseases which are regarded as treatable or preventable by use of the particular active ingredient. The dosage forms contain the particular active ingredient in the dose usual for treating the particular disease.

The production of dosage forms and preparations of the invention is described by way of example below. The following examples illustrate the invention in detail without restricting it.

EXAMPLES

Production of the Preparations (Active Ingredient Units)

Example 1

50 g of solid paraffin, 34.9 g of cetyl alcohol and 0.1 g of stearylamine are converted into a clear melt. 5.0 g of povidone is dissolved in the clear melt. At a temperature between 56-60° C. 10.0 g of pantoprazole sodium sesquihydrate is added and suspended homogeneously. The suspension is prilled in the molten state, and the drops thus produced are solidified in a cooling zone.

Example 2

55 g of solid paraffin, 30.9 g of cetyl alcohol and 0.1 g of stearylamine are converted into a clear melt. 4.0 g of povidone is dissolved in the clear melt. At a temperature between 56-60° C. 10.0 g of pantoprazole magnesium is added and suspended homogeneously. The suspension is prilled in the molten state, and the drops thus produced are solidified in a cooling zone.

Example 3

45.0 g of solid paraffin, 33.8 g of cetyl alcohol, 1.0 g of B-sitosterol and 0.2 g of stearylamine are converted into a clear melt. 1.0 g of povidone and 4.0 g of ethylcellulose are dissolved in the clear melt. At a temperature between 56-60° C. 15.0 g of pantoprazole sodium sesquihydrate is added and suspended homogeneously. The suspension is prilled in the molten state, and the drops thus produced are solidified in a cooling zone.

Example 4

52.0 g of solid paraffin, 30.3 g of cetyl alcohol and 0.2 g of stearylamine are converted into a clear melt. 5.0 g of povidone is dissolved in the clear melt. At a temperature between 56-60° C. 12.5 g of pantoprazole sodium sesquihydrate is added and suspended homogeneously. The suspension is prilled in the molten state, and the drops thus produced are solidified in a cooling zone.

Example 5

77.2 g of cetyl alcohol and 0.3 g of stearylamine are converted into a clear melt. 10.0 g of povidone is dissolved in the clear melt. At a temperature between 56-60° C. 12.5 g of pantoprazole sodium sesquihydrate is added and suspended homogeneously. The suspension is prilled in the molten state, and the drops thus produced are solidified in a cooling zone.

Example 6

47 g of solid paraffin, 40 g of glyceryltripalmitate (Dynasan 116, from Hüls) and 3 g of sitosterol are converted into a clear melt at 100° C. and cooled to 55-60° C. 10 g of lansoprazole are added and suspended homogeneously. The suspension is put in the feed container of a prilling unit (from Brace) and prilled from a 200 μm nozzle at about 0.1 bar. A periodic vibration with a frequency of about 390 Hz is transmitted to the nozzle head during this. The resulting drops are solidified in a cooling zone with air at a temperature of −30° C.

Example 7

15 g of glyceryl trimyristate (Dynasan 114), 15 grams of glyceryl tripalmitate (Dynasan 116), 50 grams of solid paraffin and 5 g of cholesterol are converted into a clear melt at about 100° C. The clear melt is cooled to about 55-65° C. 15 g of rabeprazole are added, the active ingredient is uniformly dispersed, and the homogeneous suspension is prilled as in example 6.

Example 8

10 g of glyceryl tripalmitate (Dynasan 116), 20 g of glyceryl trimyristate (Dynasan 114), 52 g of solid paraffin and 3 g of sitosterol are converted into a clear melt at about 100° C. The clear melt is cooled to 55-65° C. 15 g of omeprazole Mg are added and suspended homogeneously. The suspension is put in the feed container of a prilling unit (from Brace) and prilled through a 200 μm nozzle at 90 mbar. A periodic vibration with a frequency of about 400 Hz is transmitted to the nozzle head during this. The resulting drops are solidified with air at a temperature of −30° C. in a cooling zone.

Example 9

18 g of tristearin, 60 g of solid paraffin and 5 g of cholesterol are converted into a clear melt. The clear melt is cooled to 56-60° C. 10 g of pantoprazole sodium sesquihydrate are introduced and homogeneously dispersed. The suspension is prilled in the molten state in a prilling unit (from Brace) with vibrating nozzles, and the resulting drops are solidified in a cooling zone.

Example 10

18 g of cetyl palmitate, 40 g of solid paraffin and 2 g of cholesterol are converted into a clear melt. The clear melt is cooled to 56-60° C. 10 g of pantoprazole sodium sesquihydrate are introduced and homogenized until a uniform suspension results. The suspension is prilled in the molten state in a prilling unit (from Brace) with vibrating nozzles, and the resulting drops are solidified in a cooling zone.

Example 11

50 g of solid paraffin and 40 g of cetyl palmitate (Cutina® CP) are converted into a clear melt at 100° C. The clear melt is cooled to 50-60° C. 10 g of pantoprazole sodium sesquihydrate are introduced and suspended homogeneously. The suspension is prilled in the molten state in a prilling unit (from Brace) with vibrating nozzles (200 μm nozzle), and the resulting drops are solidified in a cooling zone.

Example 12

50 g of solid paraffin and 40 g of cetyl alcohol are converted into a clear melt at 100° C. The clear melt is cooled to 50-60° C. 10 g of pantoprazole sodium sesquihydrate are introduced and suspended homogeneously. The suspension is prilled in the molten state in a prilling unit (from Brace) with vibrating nozzles (200 μm nozzle), and the resulting drops are solidified in a cooling zone.

Example 13

50 g of solid paraffin and 40 g of glyceryl trimyristate are converted into a clear melt at 100° C. The clear melt is cooled to 50-60° C. 10 g of pantoprazole sodium sesquihydrate are introduced and suspended homogeneously. The suspension is prilled in the molten state in a prilling unit (from Brace) with vibrating nozzles (200 μm nozzle), and the resulting drops are solidified in a cooling zone.

Example 14

47 g of solid paraffin, 40 g of glyceryl tripalmitate (Dynasan 116, from Hüls) and 3 g of sitosterol are converted into a clear melt at 100° C. and cooled to 55-60° C. 10 g of lansoprazole are added and suspended homogeneously. The suspension is put into the feed container of a prilling unit (from Brace) and prilled from a 200 μm nozzle at about 0.1 bar. A periodic vibration with a frequency of about 390 Hz is transmitted to the nozzle head during this. The resulting drops are solidified in a cooling zone with air at a temperature of −30° C.

Example 15

30 g of tristearin, 60 g of solid paraffin and 4 g of sitosterol and 0.07 g stearylamine are converted into a clear melt. The clear melt is cooled to 56-60° C. 15 g of pantoprazole sodium sesquihydrate are introduced and homogeneously dispersed. The suspension is prilled in the molten state in prilling unit (from Brace) with vibrating nozzles, and the resulting drops are solidified in a cooling zone.

Example 16

17.5 g of glyceryl trimyristate (Dynasan 114), 67.5 g of solid paraffin and 5 g of cholesterol are converted into a clear melt at about 100° C. The clear melt is cooled to about 55-65° C. 10 g of pantoprazole are added, and the active ingredient is uniformly dispersed, and the homogeneous suspension is prilled as in example 6.

Example 17

98 g of cetyl alcohol and 1 g of solid paraffin are converted into a clear melt at about 90° C. 1 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 18

90 g of glyceryl monostearate are converted into a clear melt at about 90° C. 10 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 19

88 g of glyceryl myristate and 11.2 g of paraffin are converted into a clear melt at about 90° C. 0.8 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 20

96 g of cetyl alcohol and 2 g of ethylcellulose are converted into a clear melt at about 90° C. 2 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 21

84 g of glyceryl monostearate and 8 g of paraffin are converted into a clear melt at about 90° C. 8 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 22

59 g of glyceryl monostearate, 20 g of cetyl palmitate and 20 g of paraffin are converted into a clear melt at about 90° C. 1 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 23

50 g of cetyl alcohol, 5 g of glyceryl monostearate, 10 g of cetyl palmitate, 10 g of glyceryl tristearate and 24.5 g of paraffin are converted into a clear melt at about 90° C. 0.5 g of roflumilast is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 24

70 g of cetyl alcohol and 29.5 g of paraffin are converted into a clear melt at about 90° C. 0.5 g of roflumilast is added, and the mixture is stirred until it is a clear solution. The clear melt is prilled at about 75 to 80° C. in a suitable vibration prilling unit (conditions: 200 or 350 µm nozzle, pressure 100 to 170 mbar, frequency about 1 kHz).

Example 25

97.7 g of cetyl alcohol and 0.3 g of ethylcellulose are converted into a clear melt at about 90° C. 2 g of pumafentrine is added, and the mixture is stirred until it is a clear solution. The clear melt is prilled at about 75 to 80° C. in a suitable vibration prilling unit (conditions: 200 or 350 µm nozzle, pressure 100 to 170 mbar, frequency about 1 kHz).

Example 26

69 g of cetyl alcohol, 5 g of cetyl palmitate, 10 g of glyceryl tristearate and 15 g of paraffin are converted into a clear melt at about 90° C. 1 g of pumafentrine is added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 27

40 g of cetyl alcohol, 7 g of cetyl palmitate, 33 g of glyceryl tristearate and 15 g of paraffin are converted into a clear melt at about 90° C. 5 g of (7R,8R,9R)-2,3-dimethyl-8-hydroxy-7-(2-methoxyethoxy)-9-phenyl-7,8,9,10-tetrahydroimidazo[1,2-h][1,7]naphthyridine are added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 28

41 g of cetyl alcohol, 7 g of cetyl palmitate, 33 g of glyceryl tristearate and 17 g of paraffin are converted into a clear melt at about 90° C. 2 g of (7R,8R,9R)-2,3-dimethyl-8-hydroxy-7-(2-methoxyethoxy)-9-phenyl-7,8,9,10-tetrahydroimidazo[1,2-h][1,7]naphthyridine are added, and the mixture is stirred until it is a clear solution. The clear melt is prilled at about 70° C. in a suitable vibration prilling unit (conditions: 200 or 350 µm nozzle, pressure 100 to 170 mbar, frequency about 1 kHz).

Example 29

41 g of cetyl alcohol, 7 g of cetyl palmitate, 33 g of glyceryl tristearate and 17 g of paraffin are converted into a clear melt at about 90° C. 2 g of (7R,8R,9R)-2,3-dimethyl-8-hydroxy-7-(2-methoxyethoxy)-9-phenyl-7,8,9,10-tetrahydroimidazo[1,2-h][1,7]naphthyridine are added, and the mixture is stirred until it is a clear solution. The clear melt is prilled at about 70° C. in a suitable vibration prilling unit (conditions: 200 or 350 μm nozzle, pressure 100 to 170 mbar, frequency about 1 kHz).

Example 30

38 g of glyceryl tripalmitate, 2 g of cholesterol and 59.5 g of paraffin are converted into a clear melt at about 100° C. Then 0.5 g of ciclesonide is added, and the melt is prilled at about 75° C. in a suitable vibration prilling unit (conditions: 100 μm nozzle, pressure 100 to 1.70 mbar, frequency about 1.3 kHz).

Example 31

38 g of glyceryl tripalmitate, 10 g of cetyl alcohol, 2 g of cholesterol and 49.5 g of paraffin are converted into a clear melt at about 100° C. Then 0.5 g of ciclesonide is added, and the melt is prilled at about 75° C. in a suitable vibration prilling unit (conditions: 100 μm nozzle, pressure 100 to 170 mbar, frequency about 1.3 kHz).

Example 32

36 g of cetyl alcohol, 60 g of glyceryl monostearate and 2 g of vinylpyrollidone/vinyl acetate copolymer and 2 g of pumafentrine are converted into a clear melt. The clear melt is prilled at about 60° C. with a nozzle and the resulting drops are solidified by cooling.

Example 33

30 g glyceryl trimyristate, 45 g glyceryl monostearate and 20 g cetyl alcohol are converted into a clear melt. 5 g of roflumilast is added, and homogeneously dispersed. The melt is prilled at about 65° C. and the resulting drops are solidified in cooling zone.

Example 34

80 g cetostearyl alcohol, 0.5 g sodium stearate, 5 g of vinylpyrollidone/vinyl acetate copolymer and 12.5 g of glycerol trimyristate are converted into a clear melt at about 70° C. 2 g of (7R,8R,9R)-2,3-dimethyl-8-hydroxy-7-(2-methoxyethoxy)-9-phenyl-7,8,9,10-tetrahydroimidazo[1,2-h][1,7]naphthyridine is added at 60° C. and dispersed homogeneously. The mixture is prilled at 60° C. and the resulting drops solidified in a cooling zone.

Example 35

20 g glyceryl trimyristate, 14.5 g glyceryl monostearate, 60 g cetyl alcohol and 5 g vinylpyrollidone/vinyl acetate copolymer are converted into a clear melt at 70° C. 0.5 g of ciclesonide is added and homogeneously dispersed. The clear melt is prilled and the resulting drops are solidified in cooling zone.

Example 36

56.7 g of cetyl alcohol, 3 g of vinylpyrollidone/vinyl acetate copolymer, 15 g of solid paraffin, 15 g of cetyl palmitate and 0.1 g of sodium stearate are converted into a clear melt. At a temperature between 56-60° C. 10.0 g of pantoprazole sodium sesquihydrate is added and suspended homogeneously. The suspension is prilled in the molten state at 60° C. and the drops thus produced are solidified in a cooling zone.

Example 37

46.7 g of cetostearylic alcohol, 4 g of vinylpyrollidone/vinyl acetate copolymer, 23 g solid paraffin, 0.3 g of sodium stearate and 1 g sitosterol are converted into a clear melt. At a temperature between 60-65° C. 10.0 g of pantoprazole sodium sesquihydrate is added and suspended homogeneously. The suspension is prilled in the molten state at 60 to 65° C. and the drops thus produced are solidified in a cooling zone.

Example 38

39.9 g of cetyl alcohol, 3 g of vinylpyrollidone/vinyl acetate copolymer, 20 g of cetyl palmitate, 2 g cholesterol, 17 g solid paraffin and 0.1 g of sodium stearate are converted into a clear melt. At a temperature between 56-60° C. 18.0 g of pantoprazole sodium sesquihydrate is added and suspended-homogeneously. The suspension is prilled in the molten state at 60° C. and the drops thus produced are solidified in a cooling zone.

Example 39

47.9 g cetostearylic alcohol, 2 g of vinylpyrollidone/vinyl acetate copolymer, 25 g of cetyl palmitate, 1 g sitosterol, 15 g solid paraffin and 0.1 g of sodium stearate are converted into a clear melt. At a temperature between 56-60° C. 15.0 g of pantoprazole sodium sesquihydrate is added and suspended homogeneously. The suspension is prilled in the molten state at 60° C. and the drops thus produced are solidified in a cooling zone.

The preparations obtained as in examples 1-39 have a particle size in the range 50-700 μm. It is possible, for example by varying the processing conditions, to obtain larger particles.

Production of the Dosage Forms

Example A 134.7 g of mannitol, 30 g of Kollidon® 30 and 20 g of xanthan are mixed dry. The mixture is granulated with water in a fluidized bed granulator. Granules with a particle size of 0.8-1.5 mm are obtained and are mixed with the preparation (125 g) obtained as in example 1. The mixture obtained in this way is packed into bags (sachet) or—if required together with further tablet excipients—compressed to tablets in a manner known to the skilled worker.

Example B

An amount which corresponds to 22.6 mg of pantoprazole magnesium of the preparation obtained as in example 2 is mixed with 500 mg of lactose and 100 mg of xanthan. The mixture is then mixed with flavoring substances (sweetener, flavor) depending on the individual sense of taste, and thereafter packed in a bag (sachet). A suspension for oral intake is obtained by dissolving the contents of a bag in a glass of water with stirring.

Example C

An amount corresponding to 45.2 mg of pantoprazole sodium sesquihydrate of the preparation from example 3 is mixed with the appropriate amount of lactose. This mixture is mixed with a mixture of citric acid and sodium carbonate. After addition of a suitable lubricant (for example sodium stearyl fumarate) and addition of one or more suitable flavoring substances, the resulting mixture is compressed directly (without further granulation) to an effervescent tablet. A suspension for oral intake is obtained by dissolving a tablet in a glass of water.

Example D

An amount corresponding to 45.2 mg of pantoprazole sodium sesquihydrate of the preparation of example 4 is mixed with lactose to improve the flow properties. The mixture is packed together with suitable other active ingredients (for example amoxicillin or NSAIDs in usual dosage forms) into hard gelatin capsules of a suitable size.

Example E 300 mg of lactose are added to an amount corresponding to 30 mg of lansoprazole of the preparation of example 6. The two components are mixed with citric acid and sodium carbonate and, after addition of a suitable lubricant (for example sodium stearyl fumarate) and addition of suitable flavoring substances, compressed to a tablet.

Example F 450 mg of sucrose and 300 mg of xanthan are added to an amount corresponding to 30 mg of rabeprazole of the preparation of example 7. The components are mixed, and masking flavors are added. The granules are packed into sachets. The contents of a sachet can be put into a glass of water and is ready for use after stirring.

Example G 60 grams of the preparation of example 8 are mixed dry with 140 grams of mannitol, 30 grams of Kollidon 30 and 20 grams of xanthan. The mixture is granulated with water in a fluidized bed granulator. Granules with a particle size of 0.8-1.5 mm are obtained. The mixture obtained in this way is packed into bags (sachets).

Example H 140 g of mannitol, 30 g of Kollidon 30 and 20 g of xanthan are mixed dry and then granulated with water in a fluidized bed granulator. The resulting granules are screened. The screen fraction from 0.8 to 1.5 mm is mixed with 6.98 g of preparation from example 18 and packed into bags (sachets).

Example I 5 g of a preparation of example 17 are mixed with 50 g of lactose and 8 g of xanthan. Sweeteners and flavors are added to the mixture, and it is packed into bags (sachets). A suspension ready for drinking is obtained by stirring a bag into a glass of water.

Example J 12.5 mg of a preparation from example 19 are mixed with the appropriate amount of lactose. This mixture is mixed with a mixture of sodium carbonate and citric acid. After addition of a suitable lubricant (for example sodium stearyl fumarate) and addition of flavoring substances and sweeteners, the mixture obtained in this way is directly compressed to an effervescent tablet. Placing the tablet in a glass of water results, after dissolution thereof, in a suspension ready for drinking.

Example K 100 mg of a preparation from example 20 are mixed with 1.9 g of lactose and packed into 10 hard gelatin capsules.

Example L 500 mg of a preparation from example 21 are granulated with water with 15 g of mannitol and 4 g of Kollidon. The granules sufficient for 100 single doses are packed into capsules.

Example M 1 g of a preparation from example 26 are mixed with 0.2 g of xanthan, 0.1 g of saccharin sodium, 1.5 g of mannitol and 0.3 g of dry orange flavor and packed into a sachet. The suspension after stirring into about 100 ml of water is ready for use.

Example N 200 mg of a preparation from example 27 are mixed with 670 mg of Destab95 SE, 2270 mg of Pearlitol 300 DC and 50 mg of crospovidone in a free-fall mixer. 10 mg of magnesium stearate are then added through a screen. This mixture is pressed in a tablet press.

Example O 40 mg of a preparation from example 30 are mixed with 500 mg of MagGran CC, 200 mg of Karion and 70 mg of crospovidone in a free-fall mixer. 12 mg of magnesium stearate are then added through a screen, followed by brief mixing again. The mixture obtained in this way is compressed in a tablet press.

| | |
|---|---|
| 1. Preparation from example 22 | 12.500 mg |
| 2. Lactose-1-hydrate | 172.125 mg |
| 3. Corn starch | 45.000 mg |
| 4. Polyvidon ® 25 | 12.500 mg |
| 5. Polyvidone insoluble | 12.500 mg |
| 6. Flavors | 2.500 mg |
| 7. Aspartame | 0.375 mg |
| 8. Citric acid | 2.500 mg |
| 9. Magnesium stearate | 2.500 mg |
| Total | 262.500 mg |

Production: 2. and 3. are granulated with a solution of 4. The granules are dried and screened. 5. is admixed using a free-fall mixer, and then 6. 7. and 8. are incorporated. 1. is admixed and finally 9. is briefly admixed using a free-fall mixer. The mixture obtained in this way is compressed in a tablet press.

| | |
|---|---|
| 1. Preparation from example 23 | 25.000 mg |
| 2. Cellactose ® | 229.625 mg |
| 3. Sodium carboxymethylstarch | 12.500 mg |
| 4. Flavors | 2.500 mg |

-continued

|   |   |
|---|---|
| 5. Aspartame | 0.375 mg |
| 6. Citric acid | 2.500 mg |
| 7. Magnesium stearate | 2.500 mg |
| Total | 275.000 mg |

Production: 2. and 3. are mixed. 4. 5. and 6. are incorporated. 1. is admixed and finally 9. is briefly admixed using a free-fall mixer. The mixture obtained in this way is compressed in a tablet press.

|   |   |
|---|---|
| 1. Preparation from example 22 | 12.500 mg |
| 2. Lactose-1-hydrate | 49.660 mg |
| 3. Corn starch | 13.390 mg |
| 4. Polyvidon ® K 90 | 1.300 mg |
| 5. Mannit | 32.240 mg |
| 6. PVP insoluble | 12.890 mg |
| 7. Flavors | 0.330 mg |
| 8. Magnesium stearate | 1.650 mg |
| Total | 123.960 mg |

Production: 2. and 3. are granulated with a solution of 4. The granules are dried and screened. 1. 5. 6. and 7. is admixed using a free-fall mixer, and then 8. is briefly admixed using a free-fall mixer. The mixture obtained in this way is compressed in a tablet press.

|   |   |
|---|---|
| 1. Preparation from example 22 | 12.500 mg |
| 2. Lactose-1-hydrate | 70.300 mg |
| 3. Potatoe starch | 19.480 mg |
| 4. Corn starch | 2.370 mg |
| 5. sodium carboxymethylstarch | 1.900 mg |
| 6. Flavors | 0.330 mg |
| 7. Magnesium stearate | 0.950 mg |
| Total | 105.930 mg |

Production: 2. and 3. are granulated with a solution of 4. The granules are dried and screened. 1. 5. and 6. is admixed using a free-fall mixer, and then 7. is briefly admixed using a free-fall mixer. The mixture obtained in this way is compressed in a tablet press.

The invention claimed is:

1. A preparation in which an active ingredient selected from the group of PDE4 inhibitors is essentially uniformly dispersed or dissolved in an excipient matrix comprising one or more excipients selected from the group consisting of a fatty alcohol, a triglyceride, a partial glyceride and a fatty acid ester, wherein the preparation is in the form of microspheres.

2. The preparation according to claim 1, further comprising one or more additional other pharmaceutically suitable excipients in the excipient matrix.

3. The preparation according to claim 2, further comprising one or more other excipients selected from the group consisting of polymers and sterols in the excipient matrix.

4. The preparation according to claim 1, wherein the excipient matrix comprises one or more excipients selected from the group consisting of a fatty alcohol, a triglyceride and a partial glyceride.

5. The preparation according to claim 1, wherein the excipient matrix is composed of at least one solid paraffin together with one or more excipients selected from the group consisting of a fatty alcohol, a triglyceride, a partial glyceride and a fatty acid ester.

6. The preparation according to claim 5 in which the active ingredient is i) present in a matrix composed of a mixture comprising at least one fatty alcohol and at least one solid paraffin, ii) present in a matrix composed of a mixture comprising at least one triglyceride and at least one solid paraffin, iii) present in a matrix composed of a mixture comprising at least one partial glyceride and at least one solid paraffin or iv) present in a matrix composed of a mixture comprising at least one fatty acid ester and at least one solid paraffin.

7. The preparation according to claim 1, wherein the microspheres have a particle size in the range of 50-500 µm.

8. The preparation according to claim 1, wherein the microspheres have a particle size in the range of 50-400 µm.

9. The preparation according to claim 1, wherein the partial glyceride is selected from the group consisting of glycerol monostearate, glycerol distearate, glycerol monopalmitate, glycerol dipalmitate and mixtures thereof.

10. The preparation according to claim 9, wherein the partial glyceride is glycerol monostearate.

11. The preparation according to claim 1, wherein the fatty alcohol is selected from the group consisting of cetyl alcohol, myristyl alcohol, lauryl alcohol, stearyl alcohol and mixtures thereof.

12. The preparation according to claim 11, wherein the fatty alcohol is cetyl alcohol.

13. The preparation according to claim 1, obtainable by prilling a solution or dispersion of the active ingredient in the melt of the excipients using a vibrating nozzle.

14. A method of manufacturing a preparation according to claim 1, comprising the step of prilling a solution or dispersion of the active ingredient in the melt of the excipients using a vibrating nozzle.

15. A pharmaceutical dosage form comprising a preparation as claimed in claim 1 and further comprising one or more pharmaceutical excipients.

16. The pharmaceutical dosage form according to claim 15, which is selected from the group consisting of suspensions, gels, tablets, coated tablets, multi-component tablets, effervescent tablets, rapidly disintegrating tablets, powders in sachets, coated tablets, capsules, solutions and suppositories.

17. The pharmaceutical dosage form as claimed in claim 16 in the form of a rapidly disintegrating tablet, wherein the excipients are excipients which bring about rapid disintegration of said tablet.

18. The tablet as claimed in claim 17, further comprising one or more excipients selected from the group consisting of lubricants, flavors, flavoring substances and surface-active substances.

19. The pharmaceutical dosage form according to claim 16, which is a suspension or solution.

20. A suspension or solution according to claim 19, comprising one thickener or a mixture of two or more thickeners.

* * * * *